(12) United States Patent
Holick et al.

(10) Patent No.: US 6,630,453 B1
(45) Date of Patent: Oct. 7, 2003

(54) ANDROGEN DERIVATIVES AND USES THEREOF

(75) Inventors: Michael F. Holick, Sudbury, MA (US); John Kanis, Brussels (BE)

(73) Assignee: Strakan Limited (BM)

( * ) Notice: Subject to any disclaimer, the term of this patent is extended or adjusted under 35 U.S.C. 154(b) by 0 days.

(21) Appl. No.: 09/565,122

(22) Filed: May 4, 2000

Related U.S. Application Data

(60) Provisional application No. 60/132,500, filed on May 4, 1999, and provisional application No. 60/195,294, filed on Apr. 7, 2000.

(51) Int. Cl.$^7$ .............................................. A61K 31/70
(52) U.S. Cl. ................... 514/26; 536/5; 536/6
(58) Field of Search ............................ 536/5, 6; 514/26

(56) References Cited

U.S. PATENT DOCUMENTS

| | | |
|---|---|---|
| 2,447,325 A | 8/1948 | Gallagher |
| 3,007,923 A | 11/1961 | Muller et al. |
| 3,021,347 A | 2/1962 | Allen et al. |
| 3,053,865 A | 9/1962 | Taub et al. |
| 3,104,246 A | 9/1963 | Amiard et al. |
| 3,124,571 A | 3/1964 | Ringold et al. |
| 3,126,375 A | 3/1964 | Ringold et al. |
| 3,427,300 A | 2/1969 | Sarett et al. |
| 3,721,712 A | 3/1973 | Palopoli et al. |
| 3,733,318 A | 5/1973 | Marx |
| 3,862,193 A | 1/1975 | Hirsch ..................... 260/397.3 |
| 3,917,831 A | 11/1975 | Grunwell et al. ............ 424/243 |
| 3,929,768 A | 12/1975 | Brattsand et al. |
| 3,944,576 A | 3/1976 | van den Broek et al. 260/397.5 |
| 3,966,713 A | 6/1976 | Hofmeister et al. 260/239.55 R |
| 3,983,144 A | 9/1976 | Leemhuis ................. 260/397.3 |
| 4,027,459 A | 6/1977 | Nieskens et al. |
| 4,198,435 A | 4/1980 | Richardson |
| 4,201,029 A | 5/1980 | Lerner et al. |
| 4,220,599 A | 9/1980 | van der Vies ............ 260/397.4 |
| 4,292,251 A | 9/1981 | Overbeek ................. 260/397.3 |
| 4,310,523 A | 1/1982 | Neumann |
| 4,329,296 A | 5/1982 | Tax .......................... 260/397.4 |
| 4,410,515 A | 10/1983 | Holick et al. ............... 424/180 |
| 4,418,068 A | 11/1983 | Jones |
| 4,521,410 A | 6/1985 | Holick et al. .................. 514/26 |
| 4,623,660 A | 11/1986 | Richardson |
| 4,656,187 A | 4/1987 | Black et al. |
| 4,696,949 A | 9/1987 | Toivola et al. |
| 4,803,227 A | 2/1989 | Brandes et al. |
| 4,810,486 A | 3/1989 | Kelly et al. |
| 4,851,433 A | 7/1989 | Kraus |
| 4,888,331 A | 12/1989 | Elger et al. |
| 4,894,373 A | 1/1990 | Young |
| 5,024,833 A | 6/1991 | Del Bianco et al. |
| 5,103,036 A | 4/1992 | Magnin et al. |
| 5,118,667 A | 6/1992 | Adams et al. |
| 5,134,001 A | 7/1992 | Osgood |
| 5,157,027 A | 10/1992 | Biller et al. |
| 5,183,815 A | 2/1993 | Saari et al. |
| 5,189,212 A | 2/1993 | Ruenitz |
| 5,192,525 A | 3/1993 | Yang et al. |
| 5,196,409 A | 3/1993 | Breuer et al. |
| 5,196,435 A | 3/1993 | Clemens et al. |
| 5,260,065 A | 11/1993 | Mathur et al. |
| 5,312,954 A | 5/1994 | Breuer et al. |
| 5,317,015 A | 5/1994 | Ullrich et al. |
| 5,338,731 A | 8/1994 | Breuer et al. |
| 5,360,797 A | 11/1994 | Johnson et al. |
| 5,362,720 A | 11/1994 | Labrie ........................ 514/169 |
| 5,393,763 A | 2/1995 | Black et al. |
| 5,403,829 A | 4/1995 | Lehtinen et al. |
| 5,409,911 A | 4/1995 | Tyler et al. |
| 5,418,252 A | 5/1995 | Williams |
| 5,428,181 A | 6/1995 | Sugioka et al. |
| 5,439,931 A | 8/1995 | Sales |
| 5,441,964 A | 8/1995 | Bryant et al. |
| 5,446,053 A | 8/1995 | Keohane |
| 5,446,203 A | 8/1995 | McNelis |
| 5,447,941 A | 9/1995 | Zuckerman |
| 5,455,335 A | 10/1995 | Kahne et al. |
| 5,457,117 A | 10/1995 | Black et al. |
| 5,466,810 A | 11/1995 | Godfrey |
| 5,470,883 A | 11/1995 | Stromberg |
| 5,478,847 A | 12/1995 | Draper |
| 5,484,797 A | 1/1996 | Bryant et al. |
| 5,486,511 A | 1/1996 | Weintraub et al. .......... 514/178 |
| 5,491,173 A | 2/1996 | Toivola et al. |
| 5,492,927 A | 2/1996 | Gitter et al. |
| 5,494,920 A | 2/1996 | Glasebrook et al. |
| 5,496,828 A | 3/1996 | Cullinan |
| 5,496,851 A | 3/1996 | Grinnell |
| 5,502,074 A | 3/1996 | Cullinan et al. |
| 5,508,292 A | 4/1996 | Sall et al. |
| 5,508,392 A | 4/1996 | Holick |
| 5,510,358 A | 4/1996 | Palkowitz |
| 5,512,296 A | 4/1996 | Cullinan |
| 5,514,826 A | 5/1996 | Hoard et al. |
| 5,521,198 A | 5/1996 | Zuckerman |
| 5,521,214 A | 5/1996 | Bryant et al. |
| 5,525,624 A | 6/1996 | Gitter et al. |
| 5,530,010 A | 6/1996 | Glasebrook |
| 5,534,526 A | 7/1996 | Cullinan |
| 5,540,925 A | 7/1996 | Mikulski et al. |
| 5,545,634 A | 8/1996 | Labrie ........................ 514/169 |

(List continued on next page.)

FOREIGN PATENT DOCUMENTS

| | | |
|---|---|---|
| AU | B-20504/83 | 5/1984 |
| EP | 0 011 372 B1 | 2/1983 |
| EP | 0 123 485 | 10/1984 |

(List continued on next page.)

OTHER PUBLICATIONS

Liggett et al., "Osteoporosis and Its Management", *Hospital Medicine*, vol. 60, No. 4, Apr. 1999.

(List continued on next page.)

*Primary Examiner*—Elli Peselev
(74) *Attorney, Agent, or Firm*—Fish & Richardson P.C.

(57) ABSTRACT

Androgen glycosides provide free, circulatory androgen on oral administration as they are subject to less, first pass breakdown by the liver.

5 Claims, 1 Drawing Sheet

U.S. PATENT DOCUMENTS

| | | | |
|---|---|---|---|
| 5,545,641 A | 8/1996 | Bruns, Jr. et al. | |
| 5,550,123 A | 8/1996 | Cullinan | |
| 5,552,416 A | 9/1996 | Keohane | |
| 5,552,417 A | 9/1996 | Dodge | |
| 5,563,054 A | 10/1996 | Briggs et al. | |
| 5,567,820 A | 10/1996 | Dodge et al. | |
| 5,569,772 A | 10/1996 | Hoard et al. | |
| 5,578,614 A | 11/1996 | Bryant et al. | |
| 5,591,753 A | 1/1997 | Black et al. | |
| 5,593,987 A | 1/1997 | Cullinan et al. | |
| 5,602,115 A | 2/1997 | Nugent | |
| 5,610,166 A | 3/1997 | Singh | |
| 5,610,167 A | 3/1997 | Cullinan | |
| 5,610,168 A | 3/1997 | Draper | |
| 5,612,317 A | 3/1997 | Holick | 514/26 |
| 5,616,571 A | 4/1997 | Daifotis et al. | |
| 5,622,975 A | 4/1997 | Singh et al. | |
| 5,629,303 A | 5/1997 | Labrie et al. | 514/169 |
| 5,629,425 A | 5/1997 | LaBell et al. | |
| 5,635,495 A | 6/1997 | White et al. | |
| 5,641,790 A | 6/1997 | Draper | |
| 5,646,137 A | 7/1997 | Black et al. | |
| 5,658,931 A | 8/1997 | Bryant et al. | |
| 5,659,087 A | 8/1997 | Aikins et al. | |
| 5,663,184 A | 9/1997 | Bryant et al. | |
| 5,668,120 A | 9/1997 | Shinoda et al. | |
| 5,672,610 A | 9/1997 | Zuckerman | |
| 5,686,467 A | 11/1997 | Bumol et al. | |
| 5,686,468 A | 11/1997 | Cullinan | |
| 5,686,476 A | 11/1997 | May | |
| 5,688,812 A | 11/1997 | Cullinan | |
| 5,691,355 A | 11/1997 | Bryant et al. | |
| 5,693,656 A | 12/1997 | Black et al. | |
| 5,698,572 A | 12/1997 | Dodge | |
| 5,700,815 A | 12/1997 | Calnek et al. | |
| 5,708,010 A | 1/1998 | Glasebrook | |
| 5,710,285 A | 1/1998 | Hauser et al. | |
| 5,719,136 A | 2/1998 | Chwalisz et al. | |
| 5,726,168 A | 3/1998 | Cullinan et al. | |
| 5,731,327 A | 3/1998 | Luke | |
| 5,731,342 A | 3/1998 | Cullinan et al. | |
| 5,747,510 A | 5/1998 | Draper | |
| 5,753,633 A | 5/1998 | Gaffar | |
| 5,753,634 A | 5/1998 | Ebetino et al. | |
| 5,753,639 A | 5/1998 | Labrie | 514/169 |
| 5,763,611 A | 6/1998 | Kaas et al. | |
| 5,770,612 A | 6/1998 | Fontana | |
| 5,795,883 A | 8/1998 | Hesch et al. | 514/172 |
| 5,807,899 A | 9/1998 | Bohlmann et al. | |
| 5,808,061 A | 9/1998 | Dodge et al. | |
| 5,811,120 A | 9/1998 | Gibson et al. | |
| 5,821,254 A | 10/1998 | Sporn et al. | |
| 5,827,844 A | 10/1998 | Cullinan et al. | |
| 5,827,892 A | 10/1998 | Löser et al. | |
| 5,843,914 A | 12/1998 | Johnson, Jr. et al. | |
| 5,843,962 A | 12/1998 | Dodge | |
| 5,843,964 A | 12/1998 | Boss | |
| 5,843,974 A | 12/1998 | Swift | |
| 5,843,984 A | 12/1998 | Clay et al. | |
| 5,844,001 A | 12/1998 | McClay et al. | |
| 5,846,976 A | 12/1998 | Batchelor et al. | |
| 5,852,059 A | 12/1998 | Thompson | |
| 5,855,905 A | 1/1999 | Oettel et al. | 424/426 |
| 5,856,314 A | 1/1999 | Kaas et al. | |
| 5,872,114 A | 2/1999 | Labrie | 514/178 |
| 5,877,219 A | 3/1999 | Wilson | |
| 5,902,582 A | 5/1999 | Hung | |
| 5,904,930 A | 5/1999 | Fischer et al. | |
| 5,908,833 A | 6/1999 | Brattsand et al. | |
| 5,935,995 A | 8/1999 | Bosslet et al. | 514/460 |
| 5,955,100 A | 9/1999 | Bosslet et al. | 424/450 |
| 5,972,383 A | 10/1999 | Gibson et al. | |
| 6,020,315 A | 2/2000 | Bosslet et al. | 514/34 |
| 6,090,843 A | 7/2000 | Bryant et al. | |
| 6,150,336 A | 11/2000 | Deninno et al. | 514/26 |

FOREIGN PATENT DOCUMENTS

| | | |
|---|---|---|
| EP | 0 595 133 A2 | 5/1994 |
| EP | 0 683 170 A1 | 11/1995 |
| EP | 0 721 956 | 7/1996 |
| EP | 0 735 141 A2 | 10/1996 |
| EP | 0795 334 A2 | 9/1997 |
| EP | 0 879 605 A2 | 11/1998 |
| EP | 0 890 643 A2 | 1/1999 |
| GB | 584062 | 12/1944 |
| GB | 916 778 | 1/1963 |
| GB | 1015396 | 12/1965 |
| GB | 1059548 | 2/1967 |
| GB | 1 175 219 | 12/1969 |
| GB | 1 338 547 | 11/1973 |
| GB | 2 265 877 A | 10/1993 |
| JP | 62-4527 | 1/1987 |
| JP | 63-7331 | 1/1988 |
| WO | WO 92/04365 | 3/1992 |
| WO | WO 92/06068 | 4/1992 |
| WO | WO 93/00123 | 1/1993 |
| WO | 93/21198 | 10/1993 |
| WO | 93/22334 | 11/1993 |
| WO | 94/15947 | 7/1994 |
| WO | WO 95/11699 | 5/1995 |
| WO | WO 95/26720 | 10/1995 |
| WO | WO 96/03995 | 2/1996 |
| WO | WO 96/40616 | 12/1996 |
| WO | WO 99/07693 | 2/1999 |
| WO | WO 00/66612 | 11/2000 |
| WO | WO 01/27127 | 4/2001 |
| WO | WO 01/27129 | 4/2001 |

OTHER PUBLICATIONS

Cunningham, G.R., et al., "Differences in steroid specificity for rat androgen binding protein and the cytoplasmic receptor," *Steroids* 33:261–276 (1979).

Cunningham, G.R., et al., "Characterization of steroid binding specificity of the androgen receptor in human foreskin fibroblasts," *Steroids* 41:617–626 (1983).

Mellor, J.D., et al., "Steroid β–D–glucosidase activity in rabbit tissues," *J. Biol. Chem.* 246:4377–4380 (1971).

Schneider, J.J., "Preparation and properties of some new steroid β–D–glucopyranosidases, β–D–glucopyranosiduronic acids, and derivatives," *Carbohyd. Res.* 17:199–207 (1971).

Tindall, D.J., et al., "Structural requirements for steroid binding to androgen binding proteins," *Int. J. Androl. Suppl.* 2d:434–448 (1978).

Becker, D., and Galili, N., "A Novel Synthesis of Protected Glucose Intermediates," *Tetrahedron Lett.* 33:4775–4778 (1992).

Catlin, D.H., "Anabolic Steroids," in *Endocrinology*—vol. 3, ed's DeGroot et al., pp. 2362–2376 (1995).

Daggett, P.R., et al., "Oral Testosterone, a Reappraisal," *Hormone Res.* 9:121–129 (1978).

Handelsman, D.J., "Testosterone and Other Androgens: Physiology, Pharmacology, and Therapeutic Use," in *Endocrinology*—vol. 3, ed's DeGroot et al., pp. 2351–2361 (1995).

Hirtotani, M., and Furuyu, T., "Biotransformation of Testosterone and Other Androgens by Suspension Cultures of *Nicotiana Tabacum* 'Bright Yellow'," *Phytochemistry* 13:2135–2142 (1974).

Kime, D.E., and Dolben, I.P., "Hormonal Changes During Induced Ovulation of the Carp, *Cyprinus carpio*," *General Comp. Endocrin.* 58:137–149 (1985).

Kočovský, P., et al., "The Synthesis of Some New Steroid Glucosides," *Collection Czechoslov. Chem. Commun.* 38:3273–3278 (1973).

Meriggola, M.C. et al., "An Oral Regimen of Cyproterone Acetate and Testosterone Undecanoate for Spermatogenic Suppression in Men," *Fert. Steril.* 68:844–850 (1997).

Vojtišková, M., et al., "Biological Activity of Hormonally Active and Non–Active Androgen Derivatives," *Intl. J. Immunopharmac.* 4:469–474 (1982).

Wu, F.C.W., et al., "Oral Progestogen Combined with Testosterone as a Potential Male Contraceptive: Additive Effects Between Desogestrel and Testosterone Enanthate in Suppression of Spermatogenesis, Pituitary–Testicular Axis, and Lipid Metabolism," *J. Clin. Endocrin. Met.* 84:112–122 (Jan. 1999).

Zhengwei, Y., et al., "Immature Spermatids are Not Prevalent in Semen From Men Who Are Receiving Androgen–Based Contraceptive Regimens," *Fert. Steril.* 69:89–95 (1998).

Althaus, et al., "Separation of some natural and synthetic corticosteroids in biological fluids and tissues by high–performance liquid chromatography" (chemical abstract No. 136023, vol. 96, No. 17, 1982).

International Search Report for PCT/GB 01/00146; mailed Dec. 5, 2001.

Mattox, et al., "Synthesis of C–21 glucosiduronates of cortisone and related corticosteroids" (chemical abstract No. 13321, vol. 71, No. 3, 1969).

Astrom, E. and Soderhall, S., "Beneficial effect of Bisphosphonate during five years of treatment of severe osteogenesis imperfecta," *Acta Paediatr.* 97:64–68, Scandinavian University Press (1998).

Bals–Pratsch et al., "Substitution of hypogonadal men with transdermal testosterone over one year" *Acta Endocrinologica*.

Becker et al., "A Novel Synthesis of Protected Glucose Intermediates" *Tetrahedron Letters* vol. 33, No. 33, pp. 4775–4778, 1992.

Bergrem et al., "Prednisolone Pharmacokinetics and Protein–binding in Patients with Portosystemic Shunt" *Scandinavian Journal of Gastroenterology* vol. 18:273–276 (1983).

Blank, M.A. et al., "Nonclinical Model for Assessing Gastric Effects of Bisphosphonates," *Digestive Diseases and Sciences* 42:281–288, Plenum Publishing Corporation (1997).

Bonjour, J.P. and Rizzoli, R., "Clodronate in Hypercalcemia of Malignancy," *Calcif. Tissue Int.* 46:s20–s25, Springer–Verlag (1990).

Clissold et al., "Budesonide A Preliminary Review of its Pharmacodynamic Properties and Therapeutic Efficacy in Asthma and Rhinitis" *Drugs* 28:485518 (1984).

Coleman, R.E., "How can we improve the treatment of bone metastasis further?" *Curr. Opin. Oncol.* 10:s7–s13, Lippincott Williams & Wilkins (1998).

Conrow et al., "Steroid Conjugates. VI. An Improved Koenigs–Knorr Synthesis of Aryl Glucuronides Using Cadmium Carbonate, a New and Effective Catalyst" *The Journal of Organic Chemistry* vol. 36, No. 7 (1971).

Cui et al., "A budesonide prodrug accelerates treatment of colitis in rats" *Gut.* 1994;35:1439–1446.

Delbarre et al., "Ellipticine Derivatives with an Affinity to the Estrogen Receptor, and Approach to Develop Intercalating Drugs with a Specific Effect on the Hormone—Dependent Breast Cancer" *J. Med. Chem.* 1985, 28, 752–761.

Delmas, P.D. et al., "Bisphosphonate Risedronate Prevents Bone Loss in Women With Artificial Menopause Due to Chemotherapy of Breast Cancer:: A Diybke–Blind, Placebo–Controlled Study," *J. Clin. Oncol.* 15:955–962, American Society of Clinical Oncology (1997).

Delmas, P.D. Woolf, A.D., "Osteoporosis: outstanding issues," *Bailliere's Clinical Rheumatol.* 11:645–649, Balilliere Tindall (1997).

Dialog File 351, Accession No. 11481631, Derwent WPI English language abstract for EP 0 795 334 A2 (Document AL2).

Dialog File 351, Accession No. 12179761, Derwent WPI English language abstract for EP 879 605 A2 (Document AM2).

Dialog File 351, Accession No. 9865543, Derwent WPI English language abstract for EP 0 595 133 A2 (Document AM1).

Dodge, J.A., et al., "Synthesis and Estrogen Receptor Binding Affinities of the Major Human Metabolites of Raloxfene (LY139481)," *Bioorg. Med. Chem.* Lett. &:993–996, Pergamon Press (1997).

Duan et al., "Estrogen–Induced c–fos Protooncogene Expression in MCF–7 Human Breast Cancer Cells: Role of Estrogen Receptor Sp1 Complex Formation" *Endocrinology* vol. 139 No. 4, 1981–1990.

Empey et al. "Synthesis of A Novel Glucocorticoid–Conjugate Which accelerates Colitis Healing Without Adrenal Suppression" *Gastroenterology*, vol. 104, No. 4, Part 2(1993).

Fedorak et al., "Colonic Delivery of Dexamethasone From a Prodrug Accelerates Healing of Colitis in Rats Without Adrenal Suppression" *Gas.*, 1995;108:1688–1699.

Fedorak, et al., "A novel colon–specific steroid prodrug enhances sodium chloride absorption in rat colitis," *The American Physiolgical Society* 1995 G210–G218.

Fernandez et al., "Altered Phenotypic Characteristics of T47D Human Breast Cancer Cells After Prolonged Growth in Estrogen–Deficient Medium" *Cell biology International* 1998, vol. 2, No. 9/10, 623–633.

Flanagan, A.M. and Chambers, T.J. , "Inhibition of Bone Resorption by Bisphosphonates: Interactions Between Bisphosphonates, Osteoclasts, and Bone," *Calcif. Tissue Int.* 49:407–415, Springer–Verlag (1991).

Fleisch, H., "Bisphosphonates: Pharmacology and Use in the Treatment of Tumour–Induced Hypercalcaemic and Metastatic Bone Disease," *Drugs* 42:919–944, Adis International Limited (1991).

Friend et al, "A colon–Specific Drug–Delivery System Based on Drug Glycosides and the Glycosidases of Colonic Bacteria", *J. Med. Chem* 1984, 27,261–266.

Friend et al., "Colon–Specific drug delivery from a glucoside prodrug in the guinea–pig. Efficacy Study" *Journal of Controlled Release*, 15 (1991) 47–54.

Friend et al., "Drug glycosides in oral colon–specific drug delivery" *Journal of Controlled Release*, 19 (1992) 109–120.

Friend et al., "Drug Glycosides: Potential Prodrugs for colon–Specific Drug Delivery" *J. Med. Chem.* 1985, 28,51–57.

Friend et al., "Glycoside prodrugs: novel pharmacotherapy for colonic diseases" *S.T.P. Pharma Sciences* 5 (1) 70–76 1995.

Friend et al., "Relative anti–inflammatory effect of oral dexamethasone–β–D–glucoside and dexamethasone in experimental inflammatory bowel disease in guinea–pigs" *J. Pharm. Pharmacol.* 1991, 43:353–355.

Friend et al., "Review article: issues in oral administration of locally acting glucocorticosteroids for treatment of inflammatory bowel disease" *Aliment Pharmacol Ther* 1998: 12: 591–603.

Friend, et al., "Effect of Antibiotic Pretreatment on Glycoside/Glycosidase–based Colonic Drug Delivery", *Drug Design and Delivery*, 1990, Vik, 6, pp. 311–318.

Friend, et al., "Relative Antiinflammatory Effect of Oral Dexamethasone–β–D–glucoside and Dexamethasone in Experimental IBD," *Proceed. Intern. Symp. Control. Rel. Bioact. Mater.*, 18:564–565 (1991).

Fukushima, et al., "Metabolism of Testosterone N–Acetylglucosaminide," *Steroids*, Mar. 1972, 385–409.

Ganong et al., "Endocrine Function of the Testes" *Endocrinology & Metabolism* Chapter 23, 336–339, (1979).

Goodman and Gilman's "the Pharmacological Basis of Therapeutics," $8^{th}$ ed., Gilman, A.G., et al., eds., Pergamon Press, New York, NY, pp. 13–17 (1990).

Gordon–Weeks, R. et al., "Structural aspects of the effectiveness of bisphosphonates as competitive inhibitors of the plant vacuolar proton–pumping pyrophosphatase," *Biochem. J.* 337–377, The Biochemical Society (Feb. 1999.).

Graepel et al., "Reproduction Toxicity Studies with Pamidronate" *Arzneimittel Forschung Drug Research* 42 (i), 587–688, Mai 1992.

Graham, D.Y. et al., "Primary Amino–Bisphosphonates: A New Class of Gastrotoxic Drugs–Comparison of Alendronate and Aspirin,"*Am. J. Gastroenterol.* 92:1322–1325, The American College of Gastroenterology (1997).

Green, J.R. et al., "Renal Tolerability Profile of Novel, Potent Bisphosphonates in Two Short–Term Rat Models," *Pharmacol. Toxicol.* 80:225–230, Nordic Pharmacological Society (1997).

Haeberlin et al., "In Vitro Evaluation of Dexamethasone–β–D–Glucuronide for Colon–Specific Drug Delivery," *Pharmaceutical Research*, vol. 10, No. 11, 1993.

Harnageo–theophilus et al., "Acetaminophen–Induced Proliferation of Breast Cancer Cells Involves Estrogen Receptors" *Toxicology and Applied Pharmacology* 155,273–279 (1999).

Hirotani et al., Biotransformation of Testosterone and Other Androgens By Suspension Cultures of *Nicotiana tabacum*– 'Bright Yellow' *Phytochemistry* vol. 13 pp. 2135–2142 (1974).

Hirschmann et al., "An Approach to an Improved Antiinflammatory Steroid, The Synthesis of 11β, 17–Dihydroxy–3, 20–dione–1,4–pregnadien–21–yl 2–Acetamido–2–deoxy–β–D–glucopyranoside" *Journal of the American Chemical Society* vol. 86, 3903–3904 (1964).

Holstein, S. A. et al., "Phosphonate and Biphosphonate Analogues of Farnesyl Pyrophosphate as Potential Inhibitors of Farnesyl Protein Transferase," *Bioorg. Med. Chem.* 6:687–694, Elsevier Science Ltd. (1998).

International Search Report for International Application No. PCT/GB01/00140, mailed Jun. 27, 2001.

International Search Report for PCT/GB00/03865, mailed Feb. 19, 2001.

Johnson et al., "Influence of Race or Ethnicity on Pharmacokinetics of Drugs" *Journal of Pharmaceutical Sciences* vol. 86, No. 12, (1997).

Jones et al., "An On–Line HPLC–Electrospray Ionization mass spectrometric method for the study of tamoxifen metabolism" *Journal of Chromatography A*, 722 (1996)249–255.

Jones, C.D., et al., "Antiestrogens. #. Estrogen Receptor Affinities and Antiproliferative Effects in MCF–7 Cells of Phenolic Analogues of Trioxifene, [3,4–Dihydro–2–(4–methoxyphenyl)–1–naphthalenyl] [4– [2–91–pyrrolidinyl)ethoxy]–phenyl]methanone," *J. Med. Chem.* 35:931–938, American Chemical Society (1992).

Jordan et al., "Structural Requirements for the Pharmacological Activity of Nonsteroidal Antiestrogens in Vitro" *Molecular Pharmacology*, 26:272–278 (1984).

Jusko et al., "Monitoring Prednisone and Prednisolone" *Therapeutic Drug Monitoring* 2:169–176 (1980).

Kong, "Disposition of Methylprednisolone and Its Sodium Succinate Prodrug in Vivo and in Perfused Liver of Rats: Nonlinear and Sequential First–Pass Elimination" *Journal of Pharmaceutical Sciences* vol. 80, No. 5, (1991).

Lien et al. ther.Drug Monit. 1995, 17(3), 259–65.

Lim et al., "A comparative study of tamoxifen metabolism in femal rat, mouse and human liver microsomes" *Carcinogenesis* vol. 15 No. 4 pp. 589–593, 1994.

Lim et al, "High Performance Liquid Chromatography of Tamoxifen and Metabolites in Plasma and Tissues" *Biomedical Chromatography*, vol. 7, 311–314 (1993).

Lim et al., "Identification of epoxide metabolites of tamoxifen by on–line liquid chromatography–electrospray ionization mass spectrometry" *Biochemical Society Transactions* (1994)22, 165S.

Loeb, J.A., "Functional Improvement in a Patient with Cerebral Calcinosis Using a Bisphosphonate," *Movement Disorders* 13:345–349, Movement Disorder Society (1998).

Magnetto, S. et al., "Additive Antitumor Activities of Taxoids in Combination with the Bisphosphonate Ibandronate Against Invasion and Adhesion of Human Breast Carcinoma Cells to Bone," *Int. J. Cancer* 83:263–269, Wiley–Liss, Inc. (Oct. 1999).

Matsui et al., "Comparative Studies on the Metabolic Hydrogenation of the Ring A in Testosterone and Its Conjugates by Male Rat Liver in Vitro" *Chem. Pharm. Bull.*20(9)1913–1920 (1972).

May et al., "Regulation of progesterone Receptor mRNA by Oestradiol and Antioestrogens in Breast Cancer Cell Lines" *J. steroid Biochem.* vol. 33, No. 6, pp. 1035–1041, 1989.

McCague et al. *Biochem. Pharmacol.* 1990, 39(9), 1459–65.

McClung, M.R., "New Developments in Osteoporosis," *Comp. Ther.* 23:798–803, The American Society of Contemporary Medicine and Surgery (1997).

McDougal et al., "Induction of 16α-/2-Hydroxyestrone Metabolite Ratios in MCF-7 Cells by pesticides, Carcinogens, and Antiestrogens Does Not Predict Mammary Carcinogens" Environmental Health Perspectives vol. 106, No. 4, 203–206 (1998).

McLeod et al., "A Glucocorticoid Prodrug Facilitates Normal Mucosal Function in Rat Colitis Without Adrenal Suppression" Gas. 1994;106:405–413.

McLeod et al., "Glucocorticoid—Dextran Conjugates as Potential Prodrugs for Colon–Specific Delivery: Hydrolysis in Rat Gastrointestinal Tract Contents" Journal of Pharmaceutical Sciences vol. 83, No. 9, (1994).

McLeod, et al., "Synthesis and chemical stability of glucocorticoid–dextran esters: potential prodrugs for colon–specific delivery" International Journal of Pharmaceutics, 92 (1993) 105–114.

Nambara et al., "LII. Studies On Steroid Conjugates. VII. Gas Chromatography of Steroid N–Acetylglucosaminides" Journal of Chromatography 62 (1971) 369–372.

Nitta et al., "Studies on Steroids. III, The Preparation of Steorid–21–yl–glucopyranosiduronamides." Chem. Pharm. Bull 12 (4) 450–453 (1964).

Nolen III et al., "Steady–State Pharmacokinetics of Corticosteroid Delivery From Glucuronide Prodrugs in Normal and Colitic Rats" Biopharmaceutics and Drug Disposition vol. 18:8, 681–695 (1997).

Nolen III, et al., "Budesonide–β–D–glucuronide: A Prodrug for Treatment of Ulcerative Colitis".

Nolen III, et al., "Glucuronide Prodrugs for Colonic Delivery: Steady–State Kinetics in Conventional and Colitic Rates," Proceed. Intern. Symp. Control. Rel. Bioact. Mater., 23:61–62 (1996).

O'Donnell et al. Xenobiotica Feb. 1998, 28(2), 153–166.

Patlas, N. et al., "Transplacental Effects of Bisphosphonates on Fetal Skeletal Ossification and Mineralization in Rats," Teratology 60:68–73, Wiley–Liss, Inc. (Aug. 1999).

Pauwels, "Therapeutic index for inhaled steroids" Eu Respir Rev 1997;7:50,366–368.

Pending Non–Provisional U.S. patent application No. 09/565,122, Holick and Kanis, filed May 4, 2000.

Pending Non–Provisional U.S. patent application No. 09/680,272, Holick et al., filed Oct. 6, 2000.

Pending Non–Provisional U.S. patent application No. 09/759,371, Holick et al., filed Jan. 16, 2001.

Pending U.S. patent application No. 09/680,266, filed Oct. 6, 2000.

Pending U.S. patent application No. 09/760,382, filed Jan. 16, 2001.

Poon et al. Drug Metab. Dispos. 1993, 21(6), 1119–24.

Rosen et al., "Multiple Myeloma and chronic lymphocytic leukemia" Hematologic Malignancies vol. 2 No. 4, 275–282 (1995).

Ruenitz et al., "Comparative Fates of Clomiphene and Tamoxifen in the Immature Femal Rat" Drug Metabolism and Disposition vol. 13, No. 5, 582–586 (1985).

Ruenitz et al., "Estrogenic and Antiestrogenic Activity of Monophenolic Analogues of Tamoxifen, (Z)–2–[p–(1, 2–Diphenyl–1–butenyl) phenoxy]–N,N–dimethylethylamine" J. Med Chem. 1982, 25,1056–1060.

Rungby et al., "Epidemiology of Osteoporosis: Implications for Drug Therapy" Drugs & Aging vol. 6 (pp. 421–500) 1995.

Russell, R.G.G. and Rogers, M.J., "Bisphosphonates: From the Laboratory to the Clinic and Back Again," Bone 25:97–106,Elsevier Science Inc. (Jul. 1999).

Rutgeerts et al., "A Comparison of Budesonide with Prednisolone For Active Crohn's Disease" The New England Journal of Medicine vol. 31 No. 13, 842–846 (1994).

Sauer et al., "Anomeric C–19–Steroid N–Acetylglucosaminides" The Journal of Organic Chemistry vol. 34, No. 11,(1969).

Schneider et al., "Thin–Layer Chromatography of Anomeric Steroid Tri–O–Acetyl–d–glucopyranosiduronic methyl Esters, D–Glucopyranoside Tetraacetates, and 2'–Acetamido–2'–Deoxy–Tri–O–Acetyl–D–Glucopyranosides" Journal of Chromatography 48 (1970) 509–514.

Sellers et al., "The use of pamidronate in three children with renal disease" Pediatr. Nephrol (1998) 12:778–781.

Shane, et al., "Prevention of Bone Loss After Heart Transplantation With Antiresorptive Therapy: A Pilot Study" The Journal of Heart and Lung Transplantation vol. 17 No. 11, 1089–1096 (1998).

Singer, F.R. and Minoofar, P.N., "Bisphosphonates in the Treatment of Disorders of Mineral Metabolism," Advances Endocrinol. Metabol. 6:259–288, Mosby–Year Book, Inc. 1995.

Spillman et al., "BRCA1 and BRCA2 mRNA levels are coordinately elevated in human breast cancer cells in response to estrogen" Oncogene (1996) 13,1639–1645.

Surrey, "Add–Back Therapy: Extending Safety and Efficacyof GnRH Analogues in the Gynecologic Patient" Gynecol Obstet Invest 1998;45(suppl 1):31–34.

Taburet et al, "Pharmacokinetic Optimisation of Asthma Treatment" Clin. Pharmacokinet. 26 (5):396–418, 1994.

Tozer, "Colon Drug Delivery in Perspective" PDD 7126.

Tozer, et al. "Colon–Specific delivery of Dexamethason from a Glucoside Prodrug in the Guinea Pig" Pharmaceutical Research, vol. 8, No. 4, 1991.

Tumeh, S.S., "Scintigraphy in the Evaluation of Arthropathy," Radiologic Clinics North Am. 34:215–231, W.B. Saunders Company (1996).

Watanabe et al. J. Chromatogr. 1989, 497, 169–80.

Watts, "Postmenopausal Osteoporosis" CME Review Article vol. 54, No. 8 (1999).

Wilson et al, "Systemic Boiactivity Profiles or Oral Prednisolone and Nebulized Budesonide in Adult Asthmatics" Chest 114/4/1022–1027 (1998).

Xie et al., "Estrogen Induces Adenosine Deaminase Gene Expression in MCF–7 Human Breast Cancer Cells: Role of Estrogen Receptor–Sp1 Interactions" Endocrinology vol. 140, No. 1, 219–227 (1999).

Yesil, S. et al., "Further hearing loss during osteoporosis treatment with etidronate," Postgrad. Med. J. 74:363–364, British Medical Journal Publishing Group (1998).

ANDROGEN DERIVATIVES AND USES THEREOF

This application claims the benefit, under 35 U.S.C. §119(e), of U.S. application Ser. No. 60/132,500, filed May 4, 1999 and U.S. application Ser. No. 60/195,294, filed Apr. 7, 2000; the contents of each of which is incorporated herein by reference.

BACKGROUND OF THE INVENTION

1. Field of the Invention

The present invention relates to androgen derivatives and their use in therapy.

2. Related Art

Testosterone, an anabolic androgenic C19 steroid with a hydroxy group in position 17, is the principal male sex hormone. It is either synthesised from cholesterol and secreted by the Leydig cells in the testes or formed in the adrenal cortex [Ganong, Chapter 23 in *Review of Medical Physiology*, (1979), pp. 336–339]. Testosterone is found in androgen dependent target tissues, such as the testes, kidneys, skin, liver and prostate, where it is converted to 5α-dihydrotestosterone (DHT) by 5α-reductase. DHT is required for male sexual differentiation. Testosterone is also found in the brain where it is converted to oestradiol by aromatase. This conversion permits mediation of androgenic effects which include gonadotropin secretion regulation, sexual function and protein synthesis [Handelsman, "Testosterone and Other Androgens: Physiology, Pharmacology, and Therapeutic Use," in *Endocrinology—Volume* 3, Ed's DeGroot et al., (1995), pp. 2351–2361].

Testosterone is also found in skeletal muscle. However, testosterone is not converted to DHT in skeletal muscle tissue, due to low 5α-reductase activity (Handelsman, supra). According to Catlin, anabolic androgenic steroids, such as testosterone, increase the width and cross-sectional area of muscle fibres by increasing the myofilament and myofibre number [Catlin, "Anabolic Steroids," in *Endocrinology—Volume* 3, Ed's DeGroot el al. (1995), pp. 2362–2376]. In hypogonadal men, this results in an increase in lean body mass and body weight, and a decrease in body fat [Handelsman, "Testosterone and Other Androgens: Physiology, Pharmacology, and Therapeutic Use," in *Endocrinology—Volume* 3, Ed's DeGroot et al. (1995), pp. 2351–2361; Catlin, "Anabolic Steroids," in *Endocrinology—Volume* 3, Ed's DeGroot et al. (1995), pp. 2362–2376].

Testosterone and related synthetic androgens are often used in androgen replacement therapy to obtain pharmacological androgenic effects to treat conditions such as hypogonadism. Hypogonadism may be caused by a testosterone deficiency, resulting in manifestations of androgen deficiency, such as ambiguous genitalia, sexual dysfunction, osteoporosis, flushing, delayed puberty, microphallus, anaemia, incidental biochemical diagnosis or excessive fatigability [Handelsman, "Testosterone and Other Androgens: Physiology, Pharmacology, and Therapeutic Use," in *Endocrinology—Volume* 3, Ed's DeGroot et al. (1995), pp. 2351–2361]. Androgen replacement therapy has also been used to treat muscular diseases. However, such treatment generally involves administering orally active 17α-alkylated androgens which are hepatotoxic [Handelsman, "Testosterone and Other Androgens: Physiology, Pharmacology, and Therapeutic Use," in *Endocrinology—Volume* 3, Ed's DeGroot et al. (1995), pp. 2351–2361].

In hypogonadism treatment, androgen replacement therapy often consists of administering testosterone compounds to an individual to maintain testosterone levels for a prolonged period. Testosterone is ineffective, when orally administered, due to poor intestinal absorption and rapid hepatic metabolism [Daggett et al., *Hormone Res.* 9:121–129 (1978)]. Therefore, the effects of testosterone must be obtained by alternative means including administering sublingual methyl testosterone, injecting testosterone or testosterone esters, implanting testosterone, administering oral testosterone derivatives, e.g., fluoxymesterone, or applying testosterone by transdermal means [Bals-Pratsch et al., *Acta Endocrinologica (Copenh)*, 118:7–13 (1988)]. The latter method requires large patches which can be irritating or uncomfortable when applied to the scrotum. In addition, patch application can be inconvenient and is only effective when detailed instructions are followed.

Oral testosterone derivatives include 17β-esters, 7α-methyl, 17α-alkyl or methyl, 19-normethyl and D-homoandrogens [Handelsman, "Testosterone and Other Androgens: Physiology, Pharmacology, and Therapeutic Use," in *Endocrinology—Volume* 3, Ed's DeGroot el al. (1995), pp. 2351–2361]. Other known testosterone derivatives include testosterone substituted at the C1 position with methyl, e.g., methenolone and mesterolone. However, these compounds have reduced oral potency. Compounds with substitutions in, and additions to, the A ring, e.g., oxandrolone and stanozolol, are also known (Catlin, supra).

Testosterone has also been used in combination with a progestogen to achieve reversible male contraception [Wu et al., *Journal of Clinical Endocrinology and Metabolism* 84(1): 112–122 (January 1999)].

U.S. Pat. No. 5,612,317 discloses methods of treating and preventing osteoporosis and alleviating the symptoms of menopause by administering an oestrogen glycoside or oestrogen orthoester glycoside. The compounds have the formula (I):

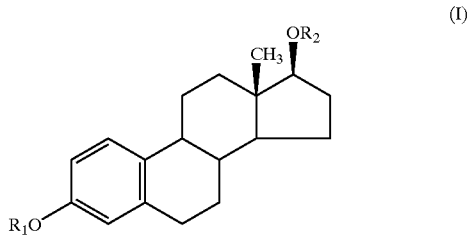

(I)

wherein $R_1$ and $R_2$ are independently hydrogen or a straight or branched chain glycosidic residue containing 1–20 glycosidic units per residue, or $R_1$ or $R_2$ is an orthoester glycoside moiety of the Formula (II):

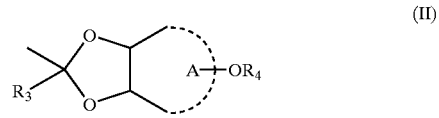

(II)

wherein A represents a glycofuranosyl or glycopyranosyl ring;

$R_3$ is hydrogen; lower $C_{1-4}$ alkyl; $C_{7-10}$ aralkyl; phenyl or phenyl substituted by chloro, fluoro, bromo, iodo, lower $C_{1-4}$ alkyl or lower $C_{1-4}$ alkoxy; or naphthyl; and $R_4$ is hydrogen or a straight or branched chain glycosidic residue containing 1–20 glycosidic units per residue;

with the further proviso that at least one of $R_1$ and $R_2$ is either a glycosidic residue or an orthoester glycoside moiety.

Hirotani and Furuya disclose the biotransformation by cultured tobacco cells of the C-19 steroid testosterone into a variety of steroid glucosides, one of which is testosterone-17-glucoside [Hirotani and Furuya, *Phytochemistry* 13: 2135–2142 (1974)].

Kocovský et al. disclose the synthesis of a variety of steroid glucosides including testosterone-17-glucoside and testosterone-17-glucoside tetraacetate [Kocovský et al., *Coll. Czech. Chem. Commun.* 38:3273–3278 (1978)].

Becker and Galili disclose the synthesis of testosterone-17-glucoside [Becker and Galili, *Tetrahedron Lett.* 33:4775–4778 (1992)].

Vojtíšková et al. disclose a study on the biological activity of testosterone-17-glucoside in mice [Vojtíšková et al., *Int. J. Immunopharmac.* 4: 469–474 (1982)]. This glucoside showed very little activity in vivo, and certainly less than testosterone administered by the same route.

It has now, surprisingly, been found that androgen glycosides taken orally are less susceptible to hepatic degradation than the corresponding unglycosylated androgen and are only substantially de-glycosylated after the first passage through the liver, thereby resulting in higher circulatory levels of the androgen. These compounds also appear to be more susceptible to gastric uptake.

SUMMARY OF THE INVENTION

The invention relates to an androgen glycoside that is not testosterone-17-β-1'-β'-D-glucopyranose.

The invention further relates to a compound having the Formula (III):

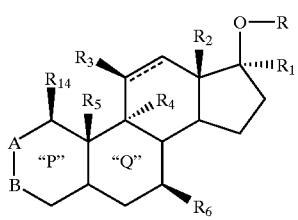

(III)

wherein the dotted line represents a single or double bond;
the rings P and Q are, independently, saturated or partially unsaturated;
R is hydrogen or a straight or branched chain glycosidic residue containing 1–20 glycosidic units per residue, or R is an orthoester glycoside moiety of the Formula (IV):

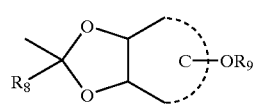

(IV)

wherein the semi-dotted ring indicated at "C" is a glycofuranosyl or glycopyranosyl ring;
$R_8$ is hydrogen; $C_{1-4}$ alkyl; $C_{7-10}$ aralkyl; phenyl; phenyl substituted by chloro, fluoro, bromo, iodo, $C_{1-4}$ alkyl or $C_{1-4}$ alkoxy; or is naphthyl;
$R_9$ is hydrogen or a straight or branched chain glycosidic residue containing 1–20 glycoside units;
$R_1$ is hydrogen, $C_{1-4}$ alkyl, $C_{2-4}$ alkenyl, $C_{2-4}$ alkynyl, $C_{1-4}$ alkanoyl or $R_1$ and R, together with the atoms to which they are attached, form a carbonyl group;

$R_2$ is hydrogen or $C_{1-4}$ alkyl;
$R_3$ is hydrogen or hydroxy;
$R_4$, where present, is hydrogen or a halogen atom;
$R_5$, where present, is hydrogen or $C_{1-4}$ alkyl;
$R_6$ is hydrogen or $C_{1-4}$ alkyl;
$R_{14}$ is hydrogen or $C_{1-4}$ alkyl;
A is oxygen, =CH, >C=CHOH, or is the group >CHR$_{13}$, wherein $R_{13}$ is hydrogen or a $C_{1-4}$ alkyl group, or A and B together form an optionally substituted pyrazole or isoxazole ring;
B is a carbonyl group, =CH, >CH$_2$>CHOR$_7$ or =C(OR$_7$)—, wherein $R_7$ is hydrogen or a straight or branched chain glycosidic residue containing 1–20 glycoside units, or $R_7$ is an orthoester glycoside moiety of the Formula (V):

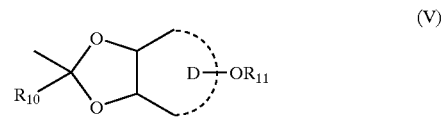

(V)

wherein the semi-dotted ring indicated at "D" represents a glycofuranosyl or glycopyranosyl ring;
$R_{10}$ is hydrogen; $C_{1-4}$ alkyl; $C_{7-10}$ aralkyl; phenyl; phenyl substituted by chloro, fluoro, bromo, iodo, $C_{1-4}$ alkyl or $C_{1-4}$ alkoxy; or is naphthyl; and
$R_{11}$ is hydrogen or a straight or branched chain glycosidic residue containing 1–20 glycoside units; and
esters thereof.

The present invention also relates to a method for treating androgen deficiency in an animal in need thereof, a method for treating hypogonadism and related conditions such as osteoporosis, sexual dysfunction and weight loss in an animal in need thereof, a method for increasing muscle mass in an animal in need thereof, a method for the treatment of a debilitating disease in an animal in need thereof and to a method of inhibiting conception in a male animal in need thereof, comprising administering to the animal an effective amount of a compound having the Formula (III):

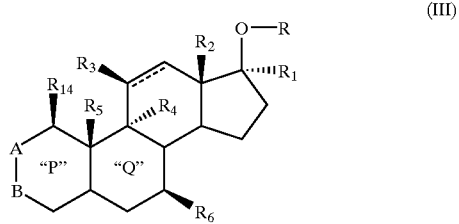

(III)

wherein the dotted line represents a single or double bond;
the rings P and Q are, independently, saturated or partially unsaturated;
R is hydrogen or a straight or branched chain glycosidic residue containing 1–20 glycosidic units per residue, or R is an orthoester glycoside moiety of the Formula (IV):

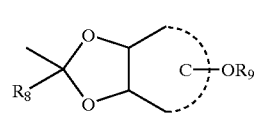

(IV)

wherein the semi-dotted ring indicated at "C" is a glycofuranosyl or glycopyranosyl ring;

$R_8$ is hydrogen; $C_{1-4}$ alkyl; $C_{7-10}$ aralkyl; phenyl; phenyl substituted by chloro, fluoro, bromo, iodo, $C_{1-4}$ alkyl or $C_{1-4}$ alkoxy; or is naphthyl;

$R_9$ is hydrogen or a straight or branched chain glycosidic residue containing 1–20 glycoside units;

$R_1$ is hydrogen, $C_{1-4}$ alkyl, $C_{2-4}$ alkenyl, $C_{2-4}$ alkynyl, $C_{1-4}$ alkanoyl or $R_1$ and R, together with the atoms to which they are attached, form a carbonyl group $R_2$ is hydrogen or $C_{1-4}$ alkyl;

$R_3$ is hydrogen or hydroxy;

$R_4$, where present, is hydrogen or a halogen atom;

$R_5$, where present, is hydrogen or $C_{1-4}$ alkyl;

$R_6$ is hydrogen or $C_{1-4}$ alkyl;

$R_{14}$ is hydrogen or $C_{1-4}$ alkyl;

A is oxygen, =CH, >C=CHOH, or is the group >CHR$_{13}$, wherein $R_{13}$ is hydrogen or a $C_{1-4}$ alkyl group, or A and B together form an optionally substituted pyrazole or isoxazole ring;

B is a carbonyl group, =CH, >CH$_2$>CHOR$_7$ or =C(OR$_7$)—, wherein $R_7$ is hydrogen or a straight or branched chain glycosidic residue containing 1–20 glycoside units, or $R_7$ is an orthoester glycoside moiety of the Formula (V):

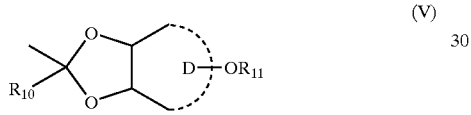

wherein the semi-dotted ring indicated at "D" represents a glycofuranosyl or glycopyranosyl ring;

$R_{10}$ is hydrogen; $C_{1-4}$ alkyl; $C_{7-10}$ aralkyl; phenyl; phenyl substituted by chloro, fluoro, bromo, iodo, $C_{1-4}$ alkyl or $C_{1-4}$ alkoxy; or is naphthyl; and $R_{11}$ is hydrogen or a straight or branched chain glycosidic residue containing 1–20 glycoside units; and esters thereof.

The invention also relates to pharmaceutical compositions comprising a compound of the present invention and a pharmaceutically acceptable carrier.

DETAILED DESCRIPTION OF THE PREFERRED EMBODIMENTS

Figure 1:
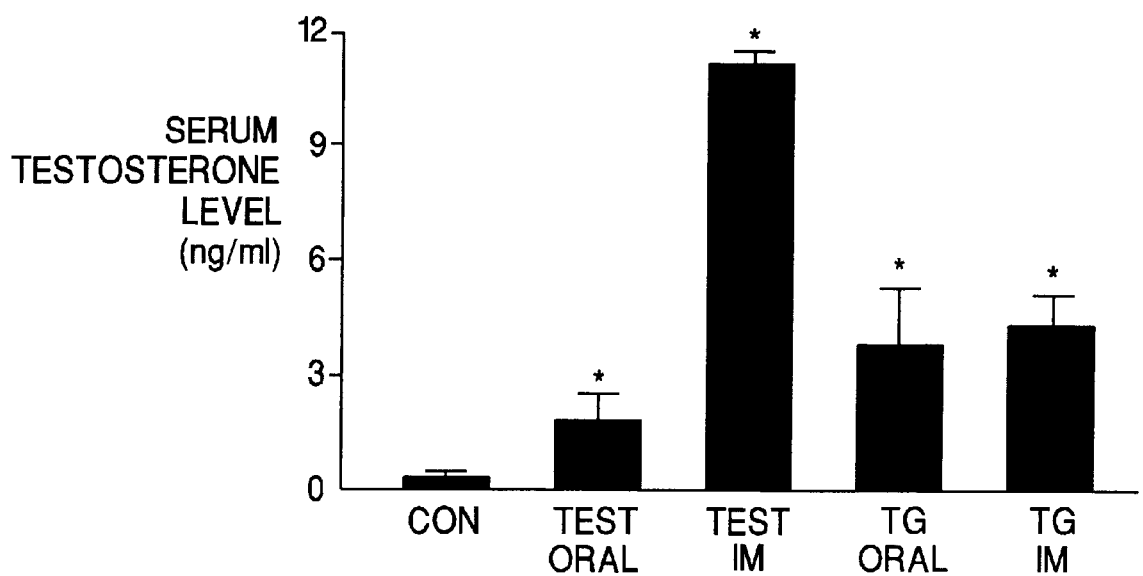
FIG. 1 is a bar graph showing the effects of injected and orally administered testosterone and testosterone-glucoside on serum testosterone levels in orchiectomized male rats.

Thus, in a first aspect, the present invention provides an androgen glycoside, other than testosterone-17-β-1'-β'-D-glucopyranose.

In an alternative aspect, the present invention provides a compound having the Formula (III):

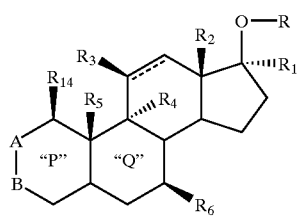

wherein the dotted line represents a single or double bond;

the rings P and Q are, independently, saturated or partially unsaturated;

R is hydrogen or a straight or branched chain glycosidic residue containing 1–20 glycosidic units per residue, or R is an orthoester glycoside moiety of the Formula (IV):

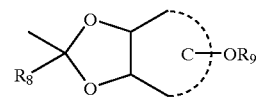

wherein the semi-dotted ring indicated at "C" is a glycofuranosyl or glycopyranosyl ring;

$R_8$ is hydrogen; $C_{1-4}$ alkyl; $C_{7-10}$ aralkyl; phenyl; phenyl substituted by chloro, fluoro, bromo, iodo, $C_{1-4}$ alkyl or $C_{1-4}$ alkoxy; or is naphthyl;

$R_9$ is hydrogen or a straight or branched chain glycosidic residue containing 1–20 glycoside units;

$R_1$ is hydrogen, $C_{1-4}$ alkyl $C_{2-4}$ alkenyl, $C_{2-4}$ alkynyl, $C_{1-4}$ alkanoyl or $R_1$ and R, together with the atoms to which they are attached, form a carbonyl group;

$R_2$ is hydrogen or $C_{1-4}$ alkyl;

$R_3$ is hydrogen or hydroxy;

$R_4$, where present, is hydrogen or a halogen atom;

$R_5$, where present, is hydrogen or $C_{1-4}$ alkyl;

$R_6$ is hydrogen or $C_{1-4}$ alkyl;

$R_{14}$ is hydrogen or $C_{1-4}$ alkyl;

A is oxygen, =CH, >C=CHOH, or is the group >CHR$_{13}$, wherein $R_{13}$ is hydrogen or a $C_{1-4}$ alkyl group, or A and B together form an optionally substituted pyrazole or isoxazole ring;

B is a carbonyl group, =CH, >CH$_2$>CHOR$_7$ or =C(OR$_7$)—, wherein $R_7$ is hydrogen or a straight or branched chain glycosidic residue containing 1–20 glycoside units, or $R_7$ is an orthoester glycoside moiety of the Formula (V):

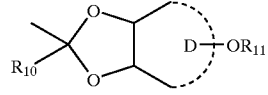

wherein the semi-dotted ring indicated at "D" represents a glycofuranosyl or glycopyranosyl ring;

$R_{10}$ is hydrogen; $C_{1-4}$ alkyl; $C_{7-10}$ aralkyl; phenyl; phenyl substituted by chloro, fluoro, bromo, iodo, $C_{1-4}$ alkyl or $C_{1-4}$ alkoxy; or is naphthyl; and $R_{11}$ is hydrogen or a straight or branched chain glycosidic residue containing 1–20 glycoside units;

and esters thereof;

provided that the compound is not an unsubstituted glucoside of testosterone, 5α-androstan-3β,17β-diol or epiandrosterone, and that, when R is hydrogen, then B is >CHOR₇ or =C(OR₇)—, and R₇ is a glycosidic residue or orthoester glycoside moiety.

It will be appreciated that the rings P and Q are never fully unsaturated, and it is preferred that the core tetracyclical structure corresponds to that of a known androgen. Where substituents are specified herein, these will, generally, preferably be with reference to such a consideration.

In the compounds of Formula (III), when A and B together form a ring, then it is preferred that the ring be a [2,3-d] isoxazole or a [3,2-c]pyrazole ring. Where present, it is preferred that C and D represent glycopyranosyl rings.

In a preferred embodiment $R_{13}$ is not hydrogen.

Where the compound is an ester, then it is preferred that it is an orthoester glycoside, preferably where at least one glycosidic residue is acylated. Acylation is preferably by a group $R_{12}$—(C=O)—, wherein $R_{12}$ is hydrogen, $C_{1-6}$ alkyl, $C_{6-10}$ substituted or unsubstituted aryl or is $C_{7-16}$ aralkyl. Particularly preferred is where $R_{12}$ is methyl.

The present invention further provides an androgen glycoside for use in therapy, and may be any compound as defined above, including testosterone glucoside. The therapy is preferably any of those described herein.

Particularly preferred compounds are 17-β-O-(1'-β'-glucopyranosyl)-3-androsterone, 5-androsten-3-β-O-(1'-β'-glucopyranosyl)-17-one and testosterone-17-β-1'-β'-D-glucopyranose.

It will be appreciated that the compounds of the invention are precursors for the free androgen.

The present invention further provides methods for treating androgen deficiency in an animal in need thereof; a method for treating hypogonadism and related conditions such as osteoporosis, sexual dysfunction and weight loss in an animal in need thereof; a method for increasing muscle mass in an animal in need thereof; and a method of inducing contraception in a male animal in need thereof; comprising administering to the animal an effective amount of a compound of the invention.

One of the potential side-effects of giving testosterone orally is its first pass biological effect on the liver. The compounds of the present invention reduce the potential for such effects. Testosterone-17β-glycoside is absorbed through the intestine and enters the portal circulation. Then, it is deposited into the systemic circulation as unmetabolised testosterone glycosides. The β-glycosidases in the body remove the β-glycoside to release free testosterone resulting in a biological effect on the target tissues.

The steroid ring system numbering is in accordance with IUPAC rules. Moreover, the valence of any given carbon in Formula III will always be 4.

The invention also provides pharmaceutical compositions comprising a compound of the present invention and a pharmaceutically acceptable carrier therefor.

It will be appreciated that the term "androgen" is well known and recognised in the art, and generally relates to any compound having an effect similar to testosterone in the mammalian, especially human, system. In particular, a compound may be considered to be an androgen if it can be used in replacement therapy in, for example, male hypogonadal disorders and other situations in which testosterone is otherwise indicated.

Preferred androgens which may be glycosylated include; boldenone, clostebol, drostanolone, epitiostanol, formebolone, mepitiostane, mesterolone, methenolone, nandrolone, oxabolone, prasterone, quinbolone, stanolone, testosterone, and trenbolone. The present invention also envisages the use of such compounds as danazol, ethyloestrenol, fluoxymesterone, furazabol, methandienone, methyltestosterone, norethandrolone, oxandrolone, oxymetholone, stanozolol. These latter compounds are 17α-alkylated compounds, and may occasionally be associated with hepatotoxicity, but it will be appreciated that any compound which serves as an androgen and which is approved for therapeutic administration may be employed in the present invention.

Glycosylation of the compounds of the present invention may be at any suitable point, but is preferably at either the 3- or 17- position. The general structure of the core of compounds of the present invention is as set out below:

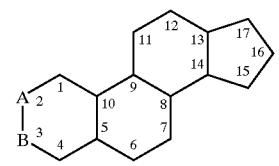

It will be appreciated that this structure is based on the cholesterol system, and any reference to ring numbering herein is with reference to the above structure.

In general, any form of glycosylation may be employed, provided that it is substantially non-toxic to the patient. Many suitable glycosidic moieties are known and preferred glycosidic moieties include the glucosides and orthoesters thereof, examples of which are given below.

More generally, the methods and compounds of the invention encompass glycosides and orthoester glycosides of steroids having androgenic activity such as those disclosed in the following U.S. Pat. Nos. 3,862,193; 3,917,831; 3,944.576; 3,966,713; 3,983,144; 4,220,599; 4,292,251; 4,329,296; 5,486,511; 5,545,634; 5,629,303; 5,753,639; 5,795,883; 5,855,905; and 5,872,114.

The invention is related in particular to the discovery that compounds of the invention can be used to treat or prevent the various conditions described herein.

In preferred embodiments, $R_1$ is hydrogen, methyl, ethyl, ethynyl, or $R_1$ and R, together with the atoms to which they are attached, form a carbonyl group; $R_2$ is methyl; $R_3$ is hydrogen or hydroxy; $R_4$ is hydrogen or fluorine; $R_5$ is nothing, hydrogen or methyl; $R_6$ is hydrogen or methyl; A is oxygen, =CH, C=CHOH or $CH_2$; B is carbonyl, $CH_2$, =CH, or CHOH; $R_{14}$ is hydrogen or methyl; or A and B together form an [2,3-d]isoxazole or a [3,2-c]pyrazole; double bonds, whenever they are present, may be at the 1,2; 4,5; 5,6; 9,10; 11,12; or at the 5,10 positions on the steroid ring; and C and D represent glycopyranosyl rings.

In other preferred embodiments, $R_1$, $R_3$, $R_4$ and $R_6$ are hydrogen, $R_2$ and $R_5$ are methyl, A is methinyl and B is a carbonyl; $R_1$, $R_3$, $R_4$ and $R_6$ are hydrogen, $R_2$ and $R_5$ are methyl, A is methinyl and B is CHOH; $R_1$, $R_2$ and $R_5$ are methyl, $R_3$, $R_4$ and $R_6$ are hydrogen, A is methinyl and B is a carbonyl; $R_1$ is ethyl, $R_2$ is methyl, $R_3$, $R_4$, $R_5$ and $R_6$ are hydrogen and A and B are methinyl; $R_1$, $R_2$ and $R_5$ are methyl, $R_3$ is a hydroxy group, $R_4$ is fluorine, $R_6$ is hydrogen, A is methinyl and B is a carbonyl; $R_1$, $R_2$ and $R_5$ are methyl, $R_3$, $R_4$ and $R_6$ are hydrogen and A and B form a pyrazole ring; $R_1$, $R_3$, $R_4$, $R_5$ and $R_6$ are hydrogen, $R_2$ is methyl, A is methinyl and B is a carbonyl; $R_1$, $R_2$ and $R_5$ are methyl, $R_3$, $R_4$ and $R_6$ are hydrogen, A is methinyl and B is CHOH; $R_1$ and $R_2$ are methyl, $R_3$ and $R_6$ are hydrogen, $R_5$ and $R_4$ are nothing, A is methinyl, B is a carbonyl group and there is a double bond between positions 9 and 10 of the steroid ring; $R_1$, $R_2$ and $R_6$ are methyl, $R_3$, $R_4$ and $R_5$ are hydrogen, A is methinyl and B is a carbonyl group; $R_1$ is ethyl, $R_2$ is methyl, $R_3$, $R_4$, $R_5$ and $R_6$ are hydrogen, A is methinyl and B is a carbonyl group; $R_1$ is an ethynyl group, $R_2$ and $R_5$ are methyl, $R_3$, $R_4$ and $R_6$ are hydrogen and A and B form an isoxazole group; $R_1$, $R_2$ and $R_5$ are methyl, $R_3$, $R_4$ and $R_6$ are hydrogen, A is oxygen and B is a carbonyl group; $R_1$ is an acetyl group, $R_2$ and $R_5$ are methyl, $R_3$, $R_4$ and $R_6$ are hydrogen, A is $CHR_{13}$ wherein $R_{13}$ is methyl and B is a carbonyl group; $R_1$, $R_3$, $R_4$ and $R_6$ are hydrogen, $R_2$ and $R_5$ are methyl, A is $CHR_{13}$ wherein $R_{13}$ is methyl and B is a carbonyl group; $R_3$, $R_4$, and $R_6$ are hydrogen, $R_2$ and $R_5$ are methyl, there is a carbonyl at the 17-position of the steroid ring, A is $CHR_{13}$ wherein $R_{13}$ is hydrogen, B is CHOH and there is a double bond between positions 5 and 6 of the steroid ring; or R, $R_1$, $R_3$, $R_4$, and $R_6$ are hydrogen, $R_2$ and $R_5$ are methyl, A is $CHR_{13}$ wherein $R_{13}$ is hydrogen and B is a carbonyl group. It will be appreciated that the present invention contemplates each of the above preferred embodiments individually. This also applies to any lists or groups indicated as being preferred in any manner herein.

Preferred compounds have a double bond between positions 4 and 5 or positions 5 and 6 of the steroid ring and single bonds in all other steroid ring positions.

Preferred compounds include, but are not limited to, testosterone-17β-glucoside, 4-androstenediol-17β-glucoside, 5α-dihydrotestosterone-17β-glucoside, methyltestosterone-17β-glucoside, ethylestrenol-17β-glucoside, fluoxymesterone-17β-glucoside, stanozolol-17β-glucoside, nandrolone-17β-glucoside, methandriol-17β-glucoside, methyltrienolone-17β-glucoside, dimethyl-19-nortestosterone-17β-glucoside, norethandrolone-17β-glucoside, danazol-17β-glucoside, oxandrolone-17β-glucoside, oxymetholone-17β-glucoside, methandrostenolone-17β-glucoside, mibolerone-17β-glucoside, boldenone-17β-glucoside, methenolone-17β-glucoside, tibolone-17β-glucoside, stanolone-17β-glucoside, prasterone-3β-glucoside, and esters, especially orthoesters, thereof. As noted above, the present invention contemplates each of the above listing individually.

Any animal which may benefit from androgen glycosides. e.g., those which have experienced or are susceptible to androgen deficiency and hypogonadism and related conditions such as osteoporosis, sexual dysfunction and weight loss, and those which have experienced or are susceptible to a decrease in muscle mass, may be treated according to the present invention. Preferred animals are humans, in particular, elderly men and women and human patients suffering from AIDS and other debilitating diseases. The phrase "debilitating diseases" is intended to encompass diseases that result in a loss or lack of strength. Upon administration of the compounds of the present invention, it is possible to reverse the adverse consequences of low muscle mass, and arrest and/or reverse the further deterioration of muscle tissue.

The compounds defined herein may also be administered to male animals as a contraceptive. In a preferred embodiment, the compounds may be combined with and/or coadministered together with a progestational compound such as progesterone [c.f. Zhengwei, Y et al. *Fert. Steril.* 69:89–95 (1998); Meriggiola, M. C. et al., *Fert. Steril.* 68:844–850 (1997); and Wu, F. C. W. et al., *J. Clin. Endocrin. Met.* 84:112–122 (1999) for related methods with testosterone and derivatives thereof]. Thus, the compounds of the invention may be administered together with the progestational compound either as separate dosage forms or as a unitary pharmaceutical composition.

By glycosidic units are meant glycopyranosyl or glycofuranosyl, as well as their amino sugar derivatives. The residues may be homopolymers, random or alternating, or block copolymers thereof. The glycosidic units have free hydroxy groups which may optionally be esterified, such as by acylation with a group $R_{12}$—(C=O)—, wherein $R_{12}$ is hydrogen, $C_{1-6}$ alkyl, $C_{6-10}$ substituted or unsubstituted aryl or $C_{7-16}$ aralkyl. Preferably, the acyl groups are acetyl or propionyl. Other preferred $R_{12}$ groups are phenyl, nitroplhenyl, halophenyl, lower alkyl substituted phenyl, lower alkoxy substituted phenyl and the like or benzyl, lower alkoxy substituted benzyl and the like.

The compounds useful in the practice of the invention contain at least one glycoside or orthoester glycoside residue, preferably at position 3 or 17. Preferably, the glycoside or orthoester glycoside is linked through the 1-carbon to the 17-position on testosterone and stanolone based molecules, and to the 3-position of prasterone based molecules.

The glycoside can comprise up to, and including, 20 glycosidic units. Preferred, however, are those having less than 10, while most preferred are those having 3 or less glycosidic units. Specific examples are those containing 1 or 2 glycosidic units in the glycoside residue.

In general, the fully or partially esterified glycoside is useful as a defined intermediate in the synthesis of the deacylated material.

Among the preferred possible glycopyranosyl structures are glucose, mannose, galactose, gulose, allose, altrose, idose, or talose. Preferred furanosyl structures are derived from fructose, arabinose or xylose. Among preferred diglycosides are sucrose, cellobiose, maltose, lactose, trehalose, gentiobiose, and melibiose. Preferred triglycosides include raffinose and gentianose. The preferred amino derivatives are N-acetyl-D-galactosamine, N-acetyl-D-glucosamine, N-acetyl-D-mannosamine, N-acetylneuraminic acid, D-glucosamine, lyxosylamine, D-galactosamine, and the like.

When more than one glycosidic unit is present on a single hydroxy group, i.e., di- or polyglycosidic residues, the individual glycosidic rings may be bonded by 1-1, 1-2, 1-3, 1-4, 1-5 or 1-6 bonds, most preferably 1-2, 1-4 and 1-6. The linkages between individual glycosidic rings may be α or β.

The water soluble glycosidic derivatives of the aforementioned compounds may be obtained according to the general methods disclosed by Holick in U.S. Pat. No. 4,410,515, the contents of which are fully incorporated by reference herein. The glycosyl orthoester compounds may be obtained according to U.S. Pat. No. 4,521,410, the contents of which are fully incorporated by reference herein. Preferred testosterone glycosyl orthoesters are testosterone-17β-(α1-D-glucopyranosyl-1',2'-orthoacetate) and testosterone-17-β-1-glucopyranosyl-1',2'-orthoacetate.

The compounds of the invention may be administered in any appropriate pharmaceutically acceptable carrier for oral administration since the testosterone glycosides and derivatives thereof are biologically active upon oral administration, which is the preferred route. The compounds of the invention may also be administered in any appropriate pharmaceutical carrier for parenteral, intramuscular or topical administration. They can be administered by any means that treat androgen deficiency and hypogonadism and related conditions such as osteoporosis, sexual dysfunction and weight loss, treat or prevent decreased muscle mass or increase muscle mass, especially in elderly humans or patients suffering from muscle debilitation, AIDS or any debilitating disease. In addition, the compounds of the present invention can be administered by any means whereby the compounds function as male contraceptives.

The dosage administered will depend on the age, health and weight of the recipient, kind of concurrent treatment, if any, frequency of treatment and the nature of the effect desired. An exemplary systemic daily dosage is about 0.001 to about 100.0 mg/kg of body weight. Normally, from about 0.01 to about 10.0 mg/kg of body weight of the glycoside or orthoester glycoside, in one or more dosages per day, is effective to obtain the desired results. One of ordinary skill in the art can determine the optimal dosages and concentrations of other active testosterone compounds and orthoester glycoside compounds with only routine experimentation.

The compounds may be employed in dosage forms such as tablets, capsules or powder packets, or liquid solutions, suspensions or elixirs for oral administration, as well as sterile liquid for formulations such as solutions or suspensions for parenteral use. A lipid vehicle can be used in parenteral administration. The compounds could also be administered via topical patches, ointments, gels or other transdermal applications. In such compositions, the active ingredient will ordinarily be present in an amount of at least 0.1% by weight based on the total weight of the composition, and not more than 90% by weight. An inert pharmaceutically acceptable carrier is preferable such as 95% ethanol, vegetable oils, propylene glycols, saline buffers, sesame oil, etc. Reference is made to *Remington's Pharmaceutical Sciences*, $18^{th}$ Edition, Gennaro el al. (eds.), 1990, for methods of preparing pharmaceutical compositions.

The invention also relates to pharmaceutical combinations comprising a compound of the invention together with a progestational compound such as progesterone, wherein each compound is present in an amount effective to induce contraception in a male animal. Such pharmaceutical compositions may also comprise a pharmaceutically acceptable carrier as described herein.

The compounds administered are preferably substantially pure, by which is meant the compounds are created by chemical synthesis and/or are substantially free of chemicals which may accompany the compounds in the natural state, as evidenced by thin layer chromatography (TLC) or high performance liquid chromatography (HPLC) (see Example 3).

It should be noted that some compounds of the present invention may exist as keto/enol isomers. Moreover, some of the compounds may exist as stereoisomers including optical isomers. The invention includes all stereoisomers and both the racemic mixtures of such stereoisomers as well as the individual enantiomers that may be separated according to methods that are well known to those of ordinary skill in the art.

The present invention will now be further illustrated by the following Examples which arc for purposes of illustration only and are not intended to be limiting unless otherwise specified. All patents, patent applications and publications cited herein are incorporated by reference in their entirety.

EXAMPLE 1

Organic Synthesis of Testosterotie-glucoside

The synthetic sequence starts from testosterone which is commercially available from Sigma Chemical Co., St. Louis, Mo. (T-1500). 4-Androsten–17-β-ol-3-one is the IUPAC name for testosterone (CAS # 58-22-0). Acetobromo-α-D-glucose; the bromo sugar used in the conjugation is commercially available through Sigma Chemical Co. (A-1750). The IUPAC name for acetobromo-α-D-glucose is 2,3,4,6-tetra-O-acetyl-α-D-glucopuranosyl bromide (CAS # 572-09-8). Cadmium salts were obtained from Aldrich Chemical Co. Inc., Milwaukee, Wis., and used without further purification. Silver fluoride and silver nitrate were purchased from Aldrich Chemical Co., Inc., and used without further purification. Hydrated sodium metasilicate, valerolactone and maleic anhydride were also purchased from Aldrich and used without further purification for the synthesis of silver silicate and silver salts of carboxylic acids. Silver silicate for the conjugation of acetobromo-α-D-glucose was prepared from silver fluoride and sodium metasilicate. Silver nitrate was used in the preparation of silver carboxylates either by the exchange of sodium anion of the carboxylate or the lanthanide salts preferably uranium carboxylates for silver anion. The silver salts were prepared freshly and dried before use.

The synthetic sequence involves conjugating testosterone with acetobromo-α-D-glucose with salts like cadmium carbonate or cadmium acetate in inert solvents like benzene, toluene or xylene wherein the starting materials and products were soluble while hot. The reactions of silver salts were performed near room temperature in chlorinated organic solvents like dichloromethane, ether or acetonitrile.

EXAMPLE 2

Testosterone-17-β-(2',3',4',6'-tetra-O-acetyl-β-D-glucopyranose) (Testosterone-glucoside Tetra-acetate)

Testosterone (2.3 g; 8 mmol) and acetobromo-α-D-glucose (3.94 g; 9.6 mmol) were added to a suspension of cadmium carbonate (2.06 g) in xylene (100 ml). The suspension was heated to reflux and stirred under an inert atmosphere for about 5 hours during which time the reaction was essentially complete. The progress of the reaction was monitored by reverse-phase TLC plates. The reaction gave a blue tinge to the cadmium surface. The reaction mixture was evaporated to remove xylenes under reduced pressure and chromatographed on silica gel and eluted with ethyl acetate and hexane resulting in the titled tetra-acetate as a crystalline solid (1.1 g, from diethylether). Testosterone (1 g) was reclaimed and used in subsequent reactions without any purification.

EXAMPLE 3

Testosterone-17-β-1'-β'-D-glucopyranose: Testosterone Glucoside

A mixture of testosterone (5.76 g; 20 mmol) and acetobromo-α-D-glucose (9.86 g; 24 mmol) was added to freshly prepared dry cadmium acetate (from 5.4 g of dihydrate; 20 mmol) suspended in dry benzene (85 ml). The mixture was refluxed for 3 hours during which time it was found that the reaction was essentially complete. There was a distinct purplish tinge to the cadmium surface during the onset of the reaction. Testosterone (3.2 g) and testosterone tetra-acetate (2.6 g) were obtained as white solids after chromatography.

1 g of tetra-acetate of testosterone-glucoside was dissolved in 80 ml of methanol and 4 g of Dowex 550A-OH resin were added. The stirred suspension was heated to reflux for 4 hours during which time the reaction was completed. The product was isolated by filtering off the resin, evaporating off the solvents and crystallising the crude gum from ethyl acetate giving 800 mg of white crystals.

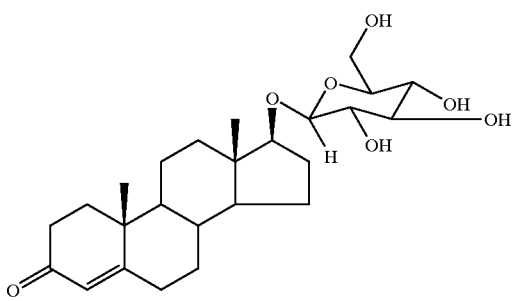

Testosterone-17-β-1'-β'-D-glucopyranose

Spectral Data

NMR spectrum of tetra-acetate of testosterone-β-glucoside:

δ 0.9 (singlet, 3H, 18 angular methyl);

δ 1.1 (singlet, 3H, angular methyl);

four overlapping singlets centred at δ 2.0 (acetate methyl groups);

multiplet δ 2.5-0.9 (20 H; $CH_2$ and CH protons);

δ 5.7 (singlet; 1H, enone);

δ 5.25 to 4.9 (three overlapping triplets 3H; coupling constant 10 hertz);

δ 4.5 (1H; doublet, coupling constant 10.2 hertz; signifying a beta glucosidic linkage);

δ 3.2-4.25 (4H; 3 protons from the sugar residue and 1H from 17 position).

NMR spectrum of testosterone 17-β-glucoside:

δ 0.9 (singlet, 3H, C18 methyl);

δ 1.1 (singlet, 3H, angular methyl);

δ 0.91-2.5 (complex multiplets for 20H, $CH_2$ and CH protons);

δ 5.8 (singlet, 1H, enone);

δ 4.3 (doublet, coupling constant 9.8 hertz, 1H, anomeric sugar hydrogen);

δ 3.2–3.9 (multiplets, 7H, 1 proton from 17 position of the steroid and rest from sugar).

Mass spectrum:

sodium ion bombardment gave a molecular ion at 473.27, i.e., corresponding to molecular weight of 450.27, which agrees with the structure.

HPLC analysis:

reverse phase HPLC using a C18 column gave a single peak. Retention time 5.04 using water:methanol mixture (2:1).

EXAMPLE 4

17-β-O-[1'-β'-Glucopyranosyl]-3-androsterone: Stanolone Glucoside

A mixture of cadmium carbonate (6 g), stanolone (2 g) and acetobromo-α-D-glucose (6.8 g), as a slurry in dry toluene (80 ml), was heated to reflux under argon. The moisture in the starting materials was azeotroped off using a Dean–Stark apparatus. The mixture was refluxed for 5 hours more. TLC examination showed the reaction was complete (2% copper sulphate solution in 10% sulphuric acid was used to stain). The reaction mixture was cooled and subjected to silica gel column chromatography. Stanolone glucoside tetraacetate (17-β-O-[1'-β'-2',3',4',6'-tetra-O-acetyl glucopyranosyl]-3-androstanone) was obtained as a gummy solid. Dry diethyl ether was added and the product crystallised out as a white solid (2.4 g).

Stanolone glucoside tetraacetate (1.8 g) and Dowex-110 OH resin (5.8 g) in methanol (60 ml) was refluxed under argon for 6 hours. The mixture was filtered while hot and the solvent was evaporated. The product crystallised as a hard solid. It was powdered and washed with 50% ethyl acetate-ether mixture. The solid was collected and dried. The product, stanolone glucoside (17-β-O-[1'-β'-glucopyranosyl]-3-androstanone), weighed 850 mg and it was found to be homogeneous by spectroscopic means.

Spectral Data

NMR spectrum of stanolone glucoside tetraacetate: ($CDCl_3$)

δ 5.3 to 3.5 (8H, sugar-H and C17-H),

δ 1.9 to 2.1 (overlapping singlets, 12H, acetates),

δ 2.4 to 0.8 (multiplets, aliphatic H, 22H),

δ 1.0 (singlet, 3H, methyl) and

δ 0.7 (singlet, 3H, C18-$CH_3$)

Mass Spectrum:

molecular ion with $Na^+$ at 643.3 amu corresponding to 620.3 amu. The theoretical value expected is 620.3 amu.

NMR spectrum of stanolone glucoside: In deuterated dimethyl sulphoxide.

δ 0.7 (singlet, 3H, $CH_3$),

δ 0.9 (singlet, 3H, $CH_3$),

δ 4.1 (doublet, anomeric coupling 8 Hz, 1H, β-linkage),

δ 0.75 to 2.5 (multiplets, aliphatic H, 22H),

δ 2.8 to 4.7 (multiplets, sugar-H and C17-H, 7H).

Mass Spectrum:

molecular ion with $Na^+$ at 475.4 amu which corresponds to 452.4 amu was obtained. The theoretical value expected is 475.4 amu

EXAMPLE 5

5-Androsten–3-β-O-(1'-β'-glucopyranosyl)-17-one: Prasterone Glucoside

A mixture of dehydroisoandrosterone (5.0 g), cadmium carbonate (13.8 g) and acetobromo-α-D-glucose (13.0 g) in toluene (200 ml) was heated to reflux under argon. The moisture from the reactants was removed using by Dean–Stark apparatus. The mixture was refluxed for an additional 5 hours. TLC examination revealed that the reaction was essentially complete. The product, as a slurry, was separated by silica gel column chromatography. The product, prasterone glucoside tetraacetate [5-androsten–3-β-O-(1'-β'-2',3',4',6'-tetra-O-acetyl)-gluco-pyranosyl-17-one) was obtained as a crystalline solid (5.9 g).

A mixture of prasterone glucoside tetraacetate (2.0 g) in methanol (60 ml) and Dowex-110-OH resin (6 g) was refluxed under argon for 8 hours. The mixture was filtered while hot and evaporated to dryness. Triturating the solid with 50% ethyl acetate-ether mixture left a white solid. The solid was filtered and washed with ether to afford 670 mg of pure prasterone glucoside (5-androsten–3-O-(1'-β-glucopyranosyl)-17-one).

Spectral Data

NMR spectrum of prasterone glucoside tetraacetate:

δ 4.52 (doublet, 7.5 Hz, anomeric-H, β-linkage),

δ 5.4-3.4 (multiplets, sugar-H, and C3-H, and C6-vinylic-H, 9H), and

δ 0.8 and 1.0 (two singlets, $CH_3$, 6H),

δ 2.0 to 2.1 (four overlapping singlets, acetates, 12H) and

δ 1.0 to 2.5 (multiplets, aliphatic-H, 19H).

Mass Spectrum:

molecular ion with $Na^+$ at 641.4 which corresponds to 618.4 amu was obtained. The theoretical value expected is 618.5 amu.

NMR spectrum of prasterone glucoside: ($d_6$-DMSO)

δ 0.8 and 0.95 (two singlets, $CH_3$, 6H),

δ 1.0 to 2.4 (multiplets, aliphatic-H, 19H),

δ 2.7 to 4.3 (multiplets, 8H, sugar-H and C3-H, and anomeric-H is a doublet, 8 Hz, at δ 4.2) and δ 5.3 (broad singlet, vinylic-H, 1H).

Mass Spectrum:

molecular ion with $Na^+$ at 473.2 which corresponds to 450.2 amu was obtained. The theoretical value expected is 450.4 amu.

EXAMPLE 6

Testosterone-17-β-1'-β'-D-glucopyranose: Testosterone Glucoside

Testosterone (1.15 g; 4 mmol) and acetobromo-α-D-glucose (1.97 g; 4.8 mmol) were added to a suspension of silver silicate (4 g; excess) in dichloromethane (50 mL). The reaction mixture was stirred for a period of 5 hours at room temperature and during this period all the testosterone was consumed. After the removal of the solids and evaporation of the solvent, the product was used as such in the deacetylation as in Example 3. The product from the deacetylation was recrystallised from ethyl acetate to afford 900 mg of the desired beta-glucosylated testosterone. The spectral characteristics of the compounds isolated in these experiments were identical to the compounds described in Examples 2 and 3.

EXAMPLE 7

5-Androsten–3-β-O-(1'-β'-glucopyranosyl)-17-one: Prasterone Glucoside

A mixture of dehydroisoandrosterone (1 g) and silver silicate (2.5 g) in dichloromethane (50 mL) was stirred at 0° C. Acetobromo-α-D-glucose (2 g) was added and the mixture was warmed to room temperature. After 3 hours the product was isolated after removing the silver salts and evaporation of the solvent. Prasterone glucoside tetra acetate was isolated almost in quantitative yield. The spectral data are identical to those of the compound described in Example 5.

EXAMPLE 8

Study to Determine the Ability of Testosterone-glucoside to Increase Serum Testosterone in Orchiectomised Rats Experimental Procedure 1. Fifteen 200 g Sprague-Dawley male rats were orchiectomised and allowed to recover for 1 week at Charles River Laboratories.

2. Rats were shipped to the Laboratory Animal Science Center at the Boston University School of Medicine, randomised, coded, weighed, and housed individually in cages for 24 hours with food and water ad libitum.

Animal Test Groups:

C=control $T_{IM}$=intramuscularly injected testosterone $T_O$=orally administered testosterone $G_{IM}$=intramuscularly injected testosterone-glucoside $G_O$=orally administered testosterone-glucoside 3. Rats were anaesthetised with ketamine and 1.5 ml of blood was removed from each animal by tail snip and the wounds were cauterised with silver nitrate.

4. Blood samples were spun to separate serum which was pipetted into new tubes and frozen at −70° C.

5. Animals were dosed daily for 6 days with 1 mg testosterone or a molar equivalent (1.56 mg) of testosterone-glucoside in 100 μl of 25% EtOH/propylene glycol by intramuscular injection or oral administration.

6. Four hours after the final dose, the rats were anaesthetised with ketamine and 5 ml of blood was removed from each animal by cardiopuncture and the carcasses sent for incineration.

7. Blood samples were spun to separate serum which was pipetted into new tubes and frozen at −70° C.

Analytical Procedure

1. Serum samples were thawed in an ice bath and 50 μl aliquots were transferred to 12×75 mm borosilicate test tubes in triplicate.

2. Aliquoted samples were applied to a testosterone radio-immunoassay (Diagnostic Systems Laboratories; Webster, Tex.) to determine serum testosterone concentrations.

3. Average serum testosterone values for each animal were determined and statistical analysis was performed on each test group to calculate means and standard deviations. These calculated values are shown in FIG. 1.

FIG. 1 is a bar graph showing the effects of injected and orally administered testosterone and testosterone-glucoside on serum testosterone levels in orchiectomised male rats. As described above, orchiectomised male rats (3 animals per group) were given 1 mg of testosterone (Test) or a molar equivalent (1.56 mg) of testosterone-glucoside (TG) in 100 μl of 25% EtOH/propylene glycol by intramuscular injection (IM) or oral administration daily for 6 days. Blood samples were taken 4 hours after the final dose. Serum testosterone levels were determined for each group by testosterone radio-immunoassay. The bars represent the mean serum testosterone levels±standard deviation for each group. * Denotes p<0.001 versus control animals.

The animals that received oral testosterone had lower blood levels of testosterone than the animals that received testosterone glucoside, orally and intramuscularly. The results demonstrate that testosterone glucoside is bioavailable when given orally, as well as intramuscularly, and is readily metabolised to testosterone.

What is claimed is:

1. A method for increasing muscle mass in an animal in need thereof, comprising orally administering to said animal an effective amount of a compound of Formula (III):

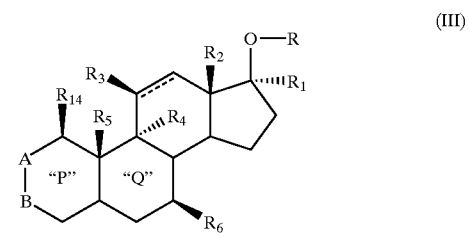

(III)

wherein the dotted line represents a single or double bond; the rings P and Q are, independently, saturated or partially unsaturated;

R is hydrogen or a straight or branched chain glycosidic residue containing 1–20 glycosidic units per residue, or R is an orthoester glycoside moiety of the Formula (IV):

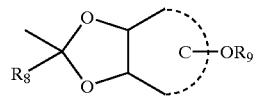

(IV)

wherein the semi-dotted ring indicated at "C" is a glycofuranosyl or glycopyranosyl ring;

$R_8$ is hydrogen; $C_{1-4}$ alkyl; $C_{7-10}$ aralkyl; phenyl; phenyl substituted by chloro, fluoro, bromo, iodo, $C_{1-4}$ alkyl or $C_{1-4}$ alkoxy; or is naphthyl;

$R_9$ is hydrogen or a straight or branched chain glycosidic residue containing 1–20 glycoside units;

$R_1$ is hydrogen, $C_{1-4}$ alkyl, $C_{2-4}$ alkenyl, $C_{2-4}$ alkynyl, $C_{1-4}$ alkanoyl or $R_1$ and R, together with the atoms to which they are attached, form a carbonyl group:

$R_2$ is hydrogen or $C_{1-4}$ alkyl;

$R_3$ is hydrogen or hydroxy;

$R_4$, where present, is hydrogen or a halogen atom;

$R_5$, where present, is hydrogen or $C_{1-4}$ alkyl;

$R_6$ is hydrogen or $C_{1-4}$ alkyl;

$R_{14}$ is hydrogen or $C_{1-4}$ alkyl;

A is oxygen, =CH, >C=CHOH, or is the group >CHR$_{13}$, wherein $R_{13}$ is hydrogen or a $C_{1-4}$ alkyl group, or A and B together form an optionally substituted pyrazole or isoxazole ring;

B is a carbonyl group, =CH, >CH$_2$>CHOR$_7$ or =C(OR$_7$)—, wherein $R_7$ is hydrogen or a straight or branched chain glycosidic residue containing 1–20 glycoside units, or $R_7$ is an orthoester glycoside moiety of the Formula (V):

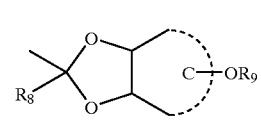

(V)

wherein the semi-dotted ring indicated at "D" represents a glycofuranosyl or glycopyranosyl ring;

$R_{10}$ is hydrogen; $C_{1-4}$ alkyl; $C_{7-10}$ aralkyl; phenyl; phenyl substituted by chloro, fluoro, bromo, iodo, $C_{1-4}$ alkyl or $C_{1-4}$ alkoxy; or is naphthyl; and $R_{11}$ is hydrogen or a straight or branched chain glycosidic residue containing 1–20 glycoside units;

and esters thereof:

provided that when R is hydrogen, then B is >CHOR$_7$ or =C(OR$_7$)—, and $R_7$ is a glycosidic residue or orthoester glycoside moiety.

2. A method for treatment of a hypogonadal disorder in an animal in need thereof, comprising orally administering to said animal an effective amount of a compound of Formula (III):

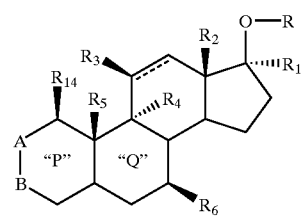

(III)

wherein the dotted line represents a single or double bond;

the rings P and Q are, independently, saturated or partially unsaturated;

R is hydrogen or a straight or branched chain glycosidic residue containing 1–20 glycosidic units per residue, or R is an orthoester glycoside moiety of the Formula (IV):

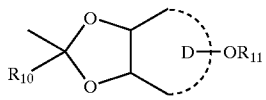

(IV)

wherein the semi-dotted ring indicated at "C" is a glycofuranosyl or glycopyranosyl ring;

$R_8$ is hydrogen; $C_{1-4}$ alkyl; $C_{7-10}$ aralkyl; phenyl; phenyl substituted by chloro, fluoro, bromo, iodo, $C_{1-4}$ alkyl or $C_{1-4}$ alkoxy; or is naphthyl;

$R_9$ is hydrogen or a straight or branched chain glycosidic residue containing 1–20 glycoside units;

$R_1$ is hydrogen, $C_{1-4}$ alkyl, $C_{2-4}$ alkenyl, $C_{2-4}$ alkynyl, $C_{1-4}$ alkanoyl or $R_1$ and R, together with the atoms to which they are attached, form a carbonyl group;

$R_2$ is hydrogen or $C_{1-4}$ alkyl;

$R_3$ is hydrogen or hydroxy;

$R_4$, where present, is hydrogen or a halogen atom;

$R_5$, where present, is hydrogen or $C_{1-4}$ alkyl;

$R_6$ is hydrogen or $C_{1-4}$ alkyl;

$R_{14}$ is hydrogen or $C_{1-4}$ alkyl;

A is oxygen, =CH, >C=CHOH, or is the group >CHR$_{13}$, wherein $R_{13}$ is hydrogen or a $C_{1-4}$ alkyl group, or A and B together form an optionally substituted pyrazole or isoxazole ring;

B is a carbonyl group, =CH, >CH$_2$>CHOR$_7$ or =C(OR$_7$)—, wherein $R_7$ is hydrogen or a straight or branched chain glycosidic residue containing 1–20 glycoside units, or $R_7$ is an orthoester glycoside moiety of the Formula (V):

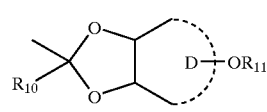

(V)

wherein the semi-dotted ring indicated at "D" represents a glycofuranosyl or glycopyranosyl ring;

$R_{10}$ is hydrogen; $C_{1-4}$ alkyl; $C_{7-10}$ aralkyl; phenyl; phenyl substituted by chloro, fluoro, bromo, iodo, $C_{1-4}$ alkyl or $C_{1-4}$ alkoxy; or is naphthyl; and $R_{11}$ is hydrogen or a straight or branched chain glycosidic residue containing 1–20 glycoside units;

and esters thereof:

provided that when R is hydrogen, then B is >CHOR₇ or =C(OR₇)—, and R₇ is a glycosidic residue or orthoester glycoside moiety.

3. A method for the treatment of androgen deficiency in an animal in need thereof, comprising orally administering to said animal an effective amount of a compound of Formula (III):

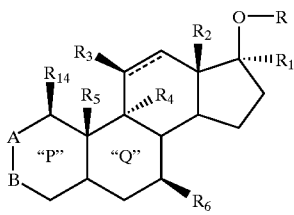

(III)

wherein the dotted line represents a single or double bond;

the rings P and Q are, independently, saturated or partially unsaturated;

R is hydrogen or a straight or branched chain glycosidic residue containing 1–20 glycosidic units per residue, or R is an orthoester glycoside moiety of the Formula (IV):

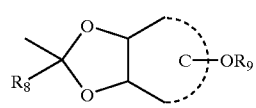

(IV)

wherein the semi-dotted ring indicated at "C" is a glycofuranosyl or glycopyranosyl ring;

$R_8$ is hydrogen; $C_{1-4}$ alkyl; $C_{7-10}$ aralkyl; phenyl; phenyl substituted by chloro, fluoro, bromo, iodo, $C_{1-4}$ alkyl or $C_{1-4}$ alkoxy; or is naphthyl;

$R_9$ is hydrogen or a straight or branched chain glycosidic residue containing 1–20 glycoside units;

$R_1$ is hydrogen, $C_{1-4}$ alkyl, $C_{2-4}$ alkenyl, $C_{2-4}$ alkynyl, $C_{1-4}$ alkanoyl or $R_1$ and R, together with the atoms to which they are attached, form a carbonyl group;

$R_2$ is hydrogen or $C_{1-4}$ alkyl;

$R_3$ is hydrogen or hydroxy;

$R_4$, where present, is hydrogen or a halogen atom;

$R_5$, where present, is hydrogen or $C_{1-4}$ alkyl;

$R_6$ is hydrogen or $C_{1-4}$ alkyl;

$R_{14}$ is hydrogen or $C_{1-4}$ alkyl;

A is oxygen, =CH, >C=CHOH, or is the group >CHR₁₃, wherein $R_{13}$ is hydrogen or a $C_{1-4}$ alkyl group, or A and B together form an optionally substituted pyrazole or isoxazole ring;

B is a carbonyl group, =CH, >CH₂>CHOR₇ or =C(OR₇)—, wherein R₇ is hydrogen or a straight or branched chain glycosidic residue containing 1–20 glycoside units, or R₇ is an orthoester glycoside moiety of the Formula (V):

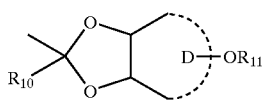

(V)

wherein the semi-dotted ring indicated at "D" represents a glycofuranosyl or glycopyranosyl ring;

$R_{10}$ is hydrogen; $C_{1-4}$ alkyl; $C_{7-10}$ aralkyl; phenyl; phenyl substituted by chloro, fluoro, bromo, iodo, $C_{1-4}$ alkyl or $C_{1-4}$ alkoxy; or is naphthyl; and $R_{11}$ is hydrogen or a straight or branched chain glycosidic residue containing 1–20 glycoside units; and esters thereof:

provided that when R is hydrogen, then B is >CHOR₇ or =C(OR₇)—, and R₇ is a glycosidic residue or orthoester glycoside moiety.

4. A method for treatment of sexual dysfunction in an animal in need thereof, comprising orally administering to said animal an effective amount of a compound of Formula (III):

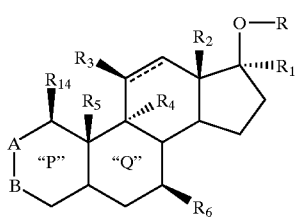

(III)

wherein the dotted line represents a single or double bond;

the rings P and Q are, independently, saturated or partially unsaturated;

R is hydrogen or a straight or branched chain glycosidic residue containing 1–20 glycosidic units per residue, or R is an orthoester glycoside moiety of the Formula (IV):

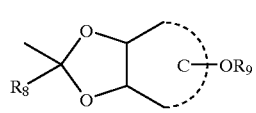

(IV)

wherein the semi-dotted ring indicated at "C" is a glycofuranosyl or glycopyranosyl ring;

$R_8$ is hydrogen; $C_{1-4}$ alkyl; $C_{7-10}$ aralkyl; phenyl; phenyl substituted by chloro, fluoro, bromo, iodo, $C_{1-4}$ alkyl or $C_{1-4}$ alkoxy; or is naphthyl;

$R_9$ is hydrogen or a straight or branched chain glycosidic residue containing 1–20 glycoside units;

$R_1$ is hydrogen, $C_{1-4}$ alkyl, $C_{2-4}$ alkenyl, $C_{2-4}$ alkynyl, $C_{1-4}$ alkanoyl or $R_1$ and R, together with the atoms to which they are attached, form a carbonyl group;

$R_2$ is hydrogen or $C_{1-4}$ alkyl;

$R_3$ is hydrogen or hydroxy;

$R_4$, where present, is hydrogen or a halogen atom;

$R_5$, where present, is hydrogen or $C_{1-4}$ alkyl;

$R_6$ is hydrogen or $C_{1-4}$ alkyl;

$R_{14}$ is hydrogen or $C_{1-4}$ alkyl;

A is oxygen, =CH, >C=CHOH, or is the group >CHR₁₃, wherein $R_{13}$ is hydrogen or a $C_{1-4}$ alkyl group, or A and B together form an optionally substituted pyrazole or isoxazole ring;

B is a carbonyl group, =CH, >CH₂>CHOR₇ or =C(OR₇)—, wherein R₇ is hydrogen or a straight or branched chain glycosidic residue containing 1–20 glycoside units, or R₇ is an orthoester glycoside moiety of the Formula (V):

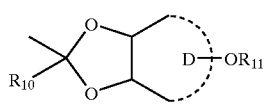
(V)

wherein the semi-dotted ring indicated at "D" represents a glycofuranosyl or glycopyranosyl ring;

$R_{10}$ is hydrogen; $C_{1-4}$ alkyl; $C_{7-10}$ aralkyl; phenyl; phenyl substituted by chloro, fluoro, bromo, iodo, $C_{1-4}$ alkyl or $C_{1-4}$ alkoxy; or is naphthyl; and $R_{11}$ is hydrogen or a straight or branched chain glycosidic residue containing 1–20 glycoside units; and esters thereof:

provided that when R is hydrogen, then B is >CHR$_7$ or =C(OR$_7$)—, and R$_7$ is a glycosidic residue or orthoester glycoside moiety.

5. A method of treating osteoporosis in an animal in need thereof, comprising orally administering to said animal an effective amount of a compound of Formula (III):

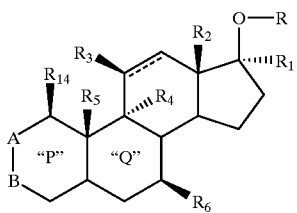
(III)

wherein the dotted line represents a single or double bond;
the rings P and Q are, independently, saturated or partially unsaturated;

R is hydrogen or a straight or branched chain glycosidic residue containing 1–20 glycosidic units per residue, or R is an orthoester glycoside moiety of the Formula (IV):

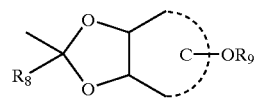
(IV)

wherein the semi-dotted ring indicated at "C" is a glycofuranosyl or glycopyranosyl ring;

$R_8$ is hydrogen; $C_{1-4}$ alkyl; $C_{7-10}$ aralkyl; phenyl; phenyl substituted by chloro, fluoro, bromo, iodo, $C_{1-4}$ alkyl or $C_{1-4}$ alkoxy; or is naphthyl;

$R_9$ is hydrogen or a straight or branched chain glycosidic residue containing 1–20 glycoside units;

$R_1$ is hydrogen, $C_{1-4}$ alkyl, $C_{2-4}$ alkenyl, $C_{2-4}$ alkynyl, $C_{1-4}$ alkanoyl or $R_1$ and R, together with the atoms to which they are attached, form a carbonyl group;

$R_2$ is hydrogen or $C_{1-4}$ alkyl;

$R_3$ is hydrogen or hydroxy;

$R_4$, where present, is hydrogen or a halogen atom;

$R_5$, where present, is hydrogen or $C_{1-4}$ alkyl;

$R_6$ is hydrogen or $C_{1-4}$ alkyl;

$R_{14}$ is hydrogen or $C_{1-4}$ alkyl;

A is oxygen, =CH, >C=CHOH, or is the group >CHR$_{13}$, wherein R$_{13}$ is hydrogen or a $C_{1-4}$ alkyl group, or A and B together form an optionally substituted pyrazole or isoxazole ring;

B is a carbonyl group, =CH, >CH$_2$>CHR$_7$ or =C(OR$_7$)—, wherein R$_7$ is hydrogen or a straight or branched chain glycosidic residue containing 1–20 glycoside units, or R$_7$ is an orthoester glycoside moiety of the Formula (V):

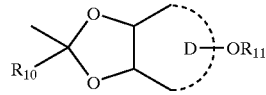
(V)

wherein the semi-dotted ring indicated at "D" represents a glycofuranosyl or glycopyranosyl ring;

$R_{10}$ is hydrogen; $C_{1-4}$ alkyl; $C_{7-10}$ aralkyl; phenyl; phenyl substituted by chloro, fluoro, bromo, iodo, $C_{1-4}$ alkyl or $C_{1-4}$ alkoxy; or is naphthyl; and $R_{11}$ is hydrogen or a straight or branched chain glycosidic residue containing 1–20 glycoside units; and esters thereof:

provided that when R is hydrogen, then B is >CHR$_7$ or =C(OR$_7$)—, and R$_7$ is a glycosidic residue or orthoester glycoside moiety.

* * * * *